US006267979B1

(12) United States Patent
Raad et al.

(10) Patent No.: US 6,267,979 B1
(45) Date of Patent: Jul. 31, 2001

(54) CHELATORS IN COMBINATION WITH BIOCIDES: TREATMENT OF MICROBIALLY INDUCED BIOFILM AND CORROSION

(75) Inventors: Issam Raad, Houston, TX (US); Robert Sherertz, Winston-Salem, NC (US)

(73) Assignees: Wake Forest University, Winston-Salem, NC (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/139,521

(22) Filed: Aug. 25, 1998

Related U.S. Application Data

(60) Provisional application No. 60/057,932, filed on Sep. 4, 1997, and provisional application No. 60/056,963, filed on Aug. 26, 1997.

(51) Int. Cl.[7] ................. A01N 25/00; C02F 5/08
(52) U.S. Cl. ............................ 424/405; 510/247
(58) Field of Search ............... 424/405; 510/247

(56) References Cited

U.S. PATENT DOCUMENTS

| 4,307,109 | * | 12/1981 | Arbir et al. | 424/405 |
| 5,435,969 | * | 7/1995 | Hoots et al. | 422/14 |
| 5,449,658 | * | 9/1995 | Unhoch et al. | 424/405 |
| 5,688,516 | * | 11/1997 | Raad et al. | 424/409 |
| 5,731,275 | * | 3/1998 | Prevost et al. | 510/161 |

OTHER PUBLICATIONS

Dorn, *Chemical Abstracts*, vol. 110, #169831, 1989.*
Garvin et al., *Chemical Abstracts*, vol. 75, #51207, 1971.*

* cited by examiner

*Primary Examiner*—Kevin E. Weddington
(74) *Attorney, Agent, or Firm*—Fulbright & Jaworski LLP

(57) ABSTRACT

Control of biofouling in pipes or aqueous systems via the use of compositions and methods that include the combination of a chelator with an antimicrobial agent.

54 Claims, 17 Drawing Sheets

CHELATORS IN COMBINATION WITH BIOCIDES: TREATMENT OF MICROBIALLY INDUCED BIOFILM AND CORROSION

This application claims the benefit of U.S. Provisional Application No. 60/057,932, filed Sep. 4, 1997, and U.S. Provisional Application No. 60/056,963, filed Aug. 26, 1997.

BACKGROUND OF THE INVENTION

1. Field of the Invention

This invention relates to a method for controlling biofouling in a variety of applications including water treatment, pulp and paper manufacture and oil field water flooding. More specifically, this invention relates to a method for controlling biofouling with a combination of an antifungal or antibiotic and a chelator.

2. Description of Related Art

Biological fouling on surfaces is a serious economic problem in many commercial and industrial aqueous process and water handling systems. For example, in 1993 North American companies spent $1.2 billion on water treatment chemicals alone to fight corrosion and fouling caused by microbial organisms embedded in biofilm attached to the surfaces of pipelines. Fouling comprises a biomass which is the buildup of microorganisms and/or extracellular substances, as well as dirt or debris that become trapped in the biomass. Bacteria, fungi, yeasts, diatoms and protozoa are only some of the organisms which cause buildup of a biomass. If not controlled, the biofouling caused by these organisms can interfere with process operations, lower the efficiency of processes, waste energy and reduce product quality.

Cooling water systems used in power-generating plants, refineries, chemical plants, air conditioning systems and other commercial and industrial operations frequently encounter biofilm problems. This is because cooling water systems are commonly contaminated with airborne organisms entrained by air/water contact in cooling towers, as well as waterborne organisms from the systems' makeup water supply. The water in such systems is generally an excellent growth medium for these organisms. If not controlled, the biofilm biofouling resulting from such growth can plug towers, block pipelines and coat heat transfer surfaces with layers of slime, and thereby prevent proper operation and reduce equipment efficiency. Furthermore, significant increases in frictional resistance to the flow of fluids through conduits affected by biofouling results in higher energy requirements to pump these fluids. In secondary oil recovery, which involves water flooding of the oil-containing formation, biofilms can plug the oil-bearing formation.

Perhaps most significantly from an economic point of view, it has recently been demonstrated that biofilms adhering to stainless steel and other metal pipeline surfaces can shift the open circuit potential of the metal, thereby accelerating the propagation rate of corrosion. Although biofilms can contain any type of microorganism, including algae, fungi and both aerobic and anaerobic bacteria, these films are often comprised of sulfate-reducing bacteria which grow anaerobically in water, frequently in the presence of oil and natural gases. Colonies that include several kinds of bacteria and fungi can form deposits on metal surfaces, building slime layers and producing organic acids that cause pitting and accelerate corrosion of pipelines and associated metal structures. Replacing corrosion-damaged pipelines and related industrial infrastructure each year represents a serious drain on the nation's, and indeed the world's economic output.

Currently used methods of controlling biofouling fall generally into two categories: chemical and abrasive. Of these methods, chemical controls are generally considered to be the most effective, both in performance and cost. However, the efficacy of chemicals where biofilms are concerned is limited by the natural defense mechanisms of the embedded microorganisms. Planktonic or free-floating organisms are readily destroyed by many chemical agents used to control microorganisms. But sessile, or fixed organisms located on pipeline surfaces, are protected by a polysaccharide covering, or glycocalyx, and will have some success in warding off the effect of even fairly toxic biocides. An increased dose of toxin may or may not succeed in overcoming the protection provided by this polysaccharide covering, because these polymers restrict permeability of the biofilm by most biocides.

A wide variety of biocides that are capable of killing planktonic microorganisms are cited in the literature; see, for example, U.S. Pat. No. 4,297,224. They include the oxidizing biocides: chlorine, bromine, chlorine dioxide, chloroisocyanurates and halogen-containing hydantoins. They also include the non-oxidizing biocides: quaternary ammonium compounds, isothiazolones, aldehydes, parabens and organo-sulfur compounds. Traditionally, the above biocides have been employed to kill planktonic microorganisms in circulating water systems such as, for example, chemical refinery cooling systems or industrial pasteurizers. Until relatively recently, little routine monitoring of biocidal efficacy versus sessile microorganisms had been performed. Studies have confirmed that many widely used biocides are relatively ineffective against sessile microorganisms; see, for example, Costerton (1988). As noted above, abrasive methods of biofouling control can also be used. These methods include simple manual removal of slime, cleaning with high pressure water streams, use of cleaning "pigs" or other methods making use of a longitudinally inserted shaft, and sand blasting. To illustrate some of the disadvantages of abrasive cleaning, consider the following technique for cleaning the interior of pipes and tubing by a device that comprises a flexible longitudinal shaft with one end connected to a circular brush and the other end connected to a motor that rotates the shaft for turning the brush. The motor is generally electrically or air driven. The device is inserted within the tube or pipe to be cleaned, and herein lies the first problem: the tubes and pipes to be cleaned are limited in length to the shaft length. In this method, the maximum pipe length is limited by the friction of the trailing flex shaft/tube casing on the inside of the pipe. The minimum tubing diameter size is approximately ¾ inch due to the required size of the flex shaft and case. Another problem is that the device is inoperable around bends of 90 degrees. Yet an additional problem is that the trailing flex-shaft and casing are very difficult to clean and maintain in a clean state under use. Also, this device is expensive to operate since it requires power such as electricity and/or shop air to run the motors in addition to, preferably, a pressurized water or cleaning solution. Other disadvantages of this and various other abrasive cleaning methods include (i) the need for protection of non-metallic surfaces such as expansion joints and valve seals, (ii) the extensive piping systems which are required for water jet cleaning, (iii) the labor-intensive nature of these methods, and (iv) the necessity of removing spent abrasive with methods such as sand blasting.

Clearly, a need exists for an effective, low toxicity method of removing and preventing water system biofouling which overcomes the disadvantages of currently known and implemented chemical and abrasive cleaning methods.

SUMMARY OF THE INVENTION

The present invention provides novel compositions and methods for controlling or reducing biofouling of pipelines, and aqueous circulating or non-circulating systems. The compositions include one or more chelators in combination with one or more biocidal or antibiotic compounds to be used to contact an area or surface susceptible to biofouling, and in some embodiments to biofouling by microorganisms.

For the purposes of this disclosure, the phrase "a chelator" denotes one or more chelators. As used herein, the term "chelator" is defined as a molecule comprising nonmetal atoms, two or more of which atoms are capable of linking or binding with a metal ion to form a heterocyclic ring including the metal ion.

For the purposes of this disclosure, the phrase "an antifungal agent" denotes one or more antifungal agents. As used herein, the term "antifungal agent" is defined as a compound having either a fungicidal or fungistatic effect upon fungi contacted by the compound.

As used herein, the term "fungicidal" is defined to mean having a destructive killing action upon fungi. As used herein, the term "fungistatic" is defined to mean having an inhibiting action upon the growth of fungi.

For the purposes of this disclosure, the phrase "an antibacterial agent" denotes one or more antibacterial agents. As used herein, the term "antibacterial agent" is defined as a compound having either a bactericidal or bacteristatic effect upon bacteria contacted by the compound.

As used herein, the term "bactericidal" is defined to mean having a destructive killing action upon bacteria As used herein, the term "bacteristatic" is defined to mean having an inhibiting action upon the growth of bacteria.

For the purposes of this disclosure, the phrase "an antimicrobial agent" denotes one or more antimicrobial agents. As used herein, the term "antimicrobial agent" is defined as a compound having either a microbicidal or microbistatic effect upon microbes or microorganisms contacted by the compound.

As used herein, the term "microbicidal" is defined to mean having a destructive killing action upon microbes or microorganisms. As used herein, the term "microbistatic" is defined to mean having an inhibiting action upon the growth of microbes or microorganisms.

As used herein the terms "microbe" or "microorganism" are defined as very minute, microscopic life forms or organisms, which may be either plant or animal, and which may include, but are not limited to, algae, bacteria, and fungi.

As used herein the terms "contact", "contacted", and "contacting", are used to describe the process by which an antimicrobial agent, e.g., any of the compositions disclosed in the present invention, comes in direct juxtaposition with the target microbe colony.

Preferable chelators for use in the present invention include, but are not limited to, ethylenediamine-N,N,N',N'-tetraacetic acid (EDTA); the disodium, trisodium, tetrasodium, dipotassium, tripotassium, dilithium and diammonium salts of EDTA; the barium, calcium, cobalt, copper, dysprosium, europium, iron, indium, lanthanum, magnesium, manganese, nickel, samarium, strontium, and zinc chelates of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis (methylenephosponic acid); O,O'-bis(2-aminoethyl) ethyleneglycol-N,N,N',N'-tetraacetic acid; N,N-bis(2-hydroxybenzyl)ethylenediamine-N,N-diacetic acid; ,1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris (methylenephosphoric acid); 7,19,30-trioxa-1,4,10,13,16, 22,27,33-octaazabicyclo [11,11,11] pentatriacontane hexahydrobromide; and triethylenetetramine-N,N,N',N'',N''',N'''-hexaacetic acid.

More preferably, the chelators for use in conjunction with the present invention may include ethylenediamine-N,N,N',N'-tetraacetic acid (EDTA); the disodium, trisodium, tetrasodium, dipotassium, tripotassium, dilithium and diammonium salts of EDTA; 1,3-diamino-2-hydroxypropane-N,N,N',N'-tetraacetic acid; 1,3-diaminopropane-N,N,N',N'-tetraacetic acid; O,O'-bis(2-aminoethyl)ethyleneglycol-N,N,N',N'-tetraacetic acid; and 7,19,30-trioxa-1,4,10,13,16,22,27,33-octaazabicyclo [11,11,11] pentatriacontane hexahydrobromide.

Most preferably, the chelators for use in the present invention may include ethylenediamine-N,N,N',N'-tetraacetic acid (EDTA); the disodium salt of EDTA; 1,3-diaminopropane-N,N,N',N'-tetraacetic acid; and O,O'-bis(2-aminoethyl)ethyleneglycol-N,N,N',N'-tetraacetic acid.

The chelators of the present invention may be delivered to an aqueous system at a dosage ranging from about 0.1 parts per million (ppm) to about 10,000 ppm, more preferably at a dosage ranging from about 1.0 ppm to about 5000 ppm, and most preferably at a dosage ranging from about 50 ppm to about 2500 ppm, including all intermediate dosages therebetween. It will be readily understood that "intermediate dosages", in these contexts, means any dosages between the quoted ranges, such as about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, 1000, etc.; 2000, 3000, 4000, 5000, 6000, 7000, 8000, 9000, and about 10,000 ppm, and including all fractional dosages therebetween.

In another embodiment, it is contemplated that the chelators of the present invention may be delivered to an aqueous system at a dosage ranging from about 200 parts per million (ppm) to about 500 ppm, including all intermediate dosages therebetween. It will be readily understood that "intermediate dosages", in these contexts, means any dosages between the quoted ranges, such as about 201, 202, 203, 204, etc.; 250, 251, 252, 253, etc.; 300, 301, 302, 303, 304, etc.; 350, 351, 352, 353, 354, etc.; 400, 401, 402, 403, 404, etc.; 450, 451, 452, 453, 454, etc.; 496, 497, 498, 499, and about 500 ppm and including all fractional dosages therebetween.

In still another embodiment, it is contemplated that the chelators of the present invention may be delivered to an aqueous system at a dosage ranging from about 500 parts per million (ppm) to about 1000 ppm, including all intermediate dosages therebetween. It will be readily understood that "intermediate dosages", in these contexts, means any dosages between the quoted ranges, such as about 501, 502, 503, 504, etc.; 550, 551, 552, 553, etc.; 600, 601, 602, 603, 604, etc.; 650, 651, 652, 653, 654, etc.; 700, 701, 702, 703, 704, etc.; 750, 751, 752, 753, 754, etc.; 801, 802, 803, 804, etc.; 850, 851, 852, 853, etc.; 900, 901, 902, 903, 904, etc.; 950, 951, 952, 953, 954, etc.; 996, 997, 998, 999 and about 1000 ppm and including all fractional dosages therebetween.

In yet another embodiment, it is contemplated that the chelators of the present invention may be delivered to an aqueous system at a dosage ranging from about 1000 parts per million (ppm) to about 5000 ppm, including all intermediate dosages therebetween. It will be readily understood that "intermediate dosages", in these contexts, means any dosages between the quoted ranges, such as about 1001, 1002, 1003, 1004, etc.; 1501, 1502, 1503, 1504, etc.; 2000, 2001, 2002, 2003, 2004, etc.; 2500, 2501, 2502, 2503, 2504, etc.; 3000, 3001, 3002, 3003, 3004, etc.; 3500, 3501, 3502, 3503, 3504, etc.; 4000, 4001, 4002, 4003, 4004, etc.; 4500, 4501, 4502, 4503, etc.; 4996, 4997, 4998, 4999 and about 5000 ppm and including all fractional dosages therebetween.

By "about" is meant "approximately" or "in the vicinity of." For example, the phrase "about 100" may mean 101, 102, 103, 104, etc., and fractional values therebetween, and it may also mean 95, 96, 97, 98, 99, etc., and fractional values therebetween.

Many antifungal agents are known to those of skill in the art and may be useful in the present invention. For example, antifungal agents contemplated for use in the present invention include, but are not limited to, new third generation triazoles such as UK 109,496 (Voriconazole); SCH 56592; ER30346; UK 9746; UK 9751; T 8581; and Flutrimazole; cell wall active cyclic lipopeptides such as Cilofungin LY121019; LY303366 (Echinocandin); and L-743872 (Pneumocandin); allylamines such as Terbinafine; imidazoles such as Omoconazole, Ketoconazole, Terconazole, Econazole, Itraconazole and Fluconazole; polyenes such as Amphotericin B, Nystatin, Natamycin, Liposomal Amphotericin B, and Liposomal Nystatin; and other antifungal agents including Griseofulvin; BF-796; MTCH 24; BTG-137586; RMP-7/Amphotericin B; Pradimicins (MNS 18184); Benanomicin; Ambisome; ABLC; ABCD; Nikkomycin Z; and Flucytosine.

More preferably, the antifungal agents for use in conjunction with the present invention may include polyenes such as Amphotericin B, Nystatin, Natamycin, Liposomal Amphotericin B, and Liposomal Nystatin; cell wall active cyclic lipopeptides such as Cilofungin LY121019; LY303366 (Echinocandin); and L-743872 (Pneumocandin); and other antifungal agents including Griseofulvin and Flucytosine.

Most preferably, the antifungal agents for use in the present invention may include Amphotericin B, Nystatin, Liposomal Amphotericin B, and Liposomal Nystatin. Preferably, the antifungal/chelator composition is introduced in amounts sufficient to kill biofouling microorganisms at film forming surfaces of the system and thereafter to maintain the concentration of the antifungal/chelator composition at a level sufficient to reduce substantially the regrowth of such microorganisms at such surfaces.

The antifungal agents of the present invention may be delivered to an aqueous system at a dosage ranging from about 0.01 parts per million (ppm) to about 1000 ppm, more preferably at a dosage ranging from about 0.1 ppm to about 100 ppm, and most preferably at a dosage ranging from about 0.5 ppm to about 10 ppm, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 150, 151, 152, 153, etc.; 500, 501, 502, 503, etc.; 600, 700, 800, 900, and about 1000 ppm, and including all fractional dosages therebetween.

In another embodiment, it is contemplated that the chelators of the present invention may be delivered to an aqueous system at a dosage ranging from about 200 parts per million (ppm) to about 500 ppm, including all intermediate dosages therebetween. It will be readily understood that "intermediate dosages", in these contexts, means any dosages between the quoted ranges, such as about 201, 202, 203, 204, etc.; 250, 251, 252, 253, etc.; 300, 301, 302, 303, 304, etc.; 350, 351, 352, 353, 354, etc.; 400, 401, 402, 403, 404, etc.; 450, 451, 452, 453, 454, etc.; 496, 497, 498, 499, and about 500 ppm and including all fractional dosages therebetween.

In still another embodiment, it is contemplated that the chelators of the present invention may be delivered to an aqueous system at a dosage ranging from about 500 parts per million (ppm) to about 1000 ppm, including all intermediate dosages therebetween. It will be readily understood that "intermediate dosages", in these contexts, means any dosages between the quoted ranges, such as about 501, 502, 503, 504, etc.; 550, 551, 552, 553, etc.; 600, 601, 602, 603, 604, etc.; 650, 651, 652, 653, 654, etc.; 700, 701, 702, 703, 704, etc.; 750, 751, 752, 753, 754, etc.; 801, 802, 803, 804, etc.; 850, 851, 852, 853, etc.; 900, 901, 902, 903, 904, etc.; 950, 951, 952, 953, 954, etc.; 996, 997, 998, 999 and about 1000 ppm and including all fractional dosages therebetween.

Because biofouling is caused by various organisms including algae, bacteria, protozoans, and the like, other types of antibiotics may also be added to the chelator/antifungal compositions described above. Such agents may include, but are not limited to aminoglycoside, ampicillin, carbenicillin, cefazolin, cephalosporin, chloramphenicol, clindamycin, erythromycin, everninomycin, gentamycin, kanamycin, lipopeptides, methicillin, nafcillin, novobiocia, oxazolidinones, penicillin, polymyxin, quinolones, rifampin, streptogramins, streptomycin, sulfamethoxazole, sulfonamide, tetracycline, trimethoprim and vancomycin.

The antibiotics of the present invention may be delivered to an aqueous system at a dosage ranging from about 0.01 parts per million (ppm) to about 1000 ppm, more preferably at a dosage ranging from about 0.1 ppm to about 100 ppm, and most preferably at a dosage ranging from about 0.5 ppm to about 10 ppm, including all intermediate dosages therebetween. It will be readily understood that "intermediate dosages", in these contexts, means any dosages between the quoted ranges, such as about 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 ppm, and including all fractional dosages therebetween.

In another embodiment, it is contemplated that the chelators of the present invention may be delivered to an aqueous system at a dosage ranging from about 200 parts per million (ppm) to about 500 ppm, including all intermediate dosages therebetween. It will be readily understood that "intermediate dosages", in these contexts, means any dosages between the quoted ranges, such as about 201, 202, 203, 204, etc.; 250, 251, 252, 253, etc.; 300, 301, 302, 303, 304, etc.; 350, 351, 352, 353, 354, etc.; 400, 401, 402, 403, 404, etc.; 450, 451, 452, 453, 454, etc.; 496, 497, 498, 499, and about 500 ppm and including all fractional dosages therebetween.

In still another embodiment, it is contemplated that the chelators of the present invention may be delivered to an aqueous system at a dosage ranging from about 500 parts per million (ppm) to about 1000 ppm, including all intermediate dosages therebetween. It will be readily understood that "intermediate dosages", in these contexts, means any dosages between the quoted ranges, such as about 501, 502, 503, 504, etc.; 550, 551, 552, 553, etc.; 600, 601, 602, 603, 604, etc.; 650, 651, 652, 653, 654, etc.; 700, 701, 702, 703, 704, etc.; 750, 751, 752, 753, 754, etc.; 801, 802, 803, 804, etc.; 850, 851, 852, 853, etc.; 900, 901, 902, 903, 904, etc.; 950, 951, 952, 953, 954, etc.; 996, 997, 998, 999 and about 1000 ppm and including all fractional dosages therebetween.

Other active agents may include additional algicides, fungicides, corrosion inhibitors, scale inhibitors, complexing agents, surfactants, enzymes, nonoxidizing biocides and other compatible products which will lend greater functionality to the product. The other active agents of the present invention may be delivered to an aqueous system at a dosage known by those skilled in the art to be efficacious.

Other biocides that may be used are: ortho-phthalaldehyde, bromine, chlorine, ozone, chlorine dioxide, chlorhexidine, chloroisocyanurates, chlorine donors, formaldehyde, glutaraldehyde, halogen-containing hydantoins, a peroxy salt (a salt which produces hydrogen peroxide in water), a percarbonate, peracetate, persulfate, peroxide, or perborate salt, quaternary ammonium compounds, isothiazolones, parabens, silver sulfonamides, and organo-sulfur compounds. The other biocides of the present invention may be delivered to an aqueous system at a dosage known by those skilled in the art to be efficacious.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the inhibitory effect of EDTA on *Apergillus flavus* in vitro.

FIG. 2 shows the inhibitory effect of EDTA on *Aspergillus terreus* in vitro.

FIG. 3 shows the inhibitory effect of EDTA on *Fusarium oxysporum* in vitro.

FIG. 4 shows the inhibitory effect of EDTA on *Candida krusei* in vitro.

FIG. 5 shows the synergistic inhibition of *Aspergillus fumigatus* by Amphotericin B and EDTA (1.0 mg/mL) in vitro.

FIG. 6 shows the synergistic inhibition of *Aspergillus fumigatus* by Amphotericin B and EDTA (0.1 mg/mL) in vitro.

FIG. 7 shows the synergistic inhibition of *Aspergillus flavus* by Amphotericin B and EDTA (1.0 mg/mL) in vitro.

FIG. 8 shows the synergistic inhibition of *Aspergillus flavus* by Amphotericin B and EDTA (0.1 mg/mL) in vitro.

FIG. 9 shows the synergistic inhibition of *Fusarium solani* by Amphotericin B and EDTA in vitro.

FIG. 10 shows the synergistic inhibition of *Aspergillus fumigatus* by Ambisome and EDTA (0.1 mg/mL) in vitro.

FIG. 11 shows the synergistic inhibition of *Fusarium solani* by Ambisome and EDTA in vitro.

FIG. 12 shows the inhibitory effect of EDTA on vanomycin resistant enterococci in vitro.

FIG. 13 shows the inhibitory effect of EDTA on multidrug resistant *S. maltophilia* in vitro.

FIG. 14 shows the inhibitory effect of EDTA on multidrug resistant Pseudomonas in vitro.

FIG. 15 shows the synergistic inhibition of vanomycin resistant enterococci by minocycline and EDTA in vitro.

FIG. 16 shows the synergistic inhibition of *S. maltophilia* by gentamycin and EDTA in vitro.

FIG. 17 shows the synergistic inhibition of *S. maltophilia* by polymyxin B and EDTA in vitro.

DESCRIPTION OF ILLUSTRATIVE EMBODIMENTS

Figure 1:
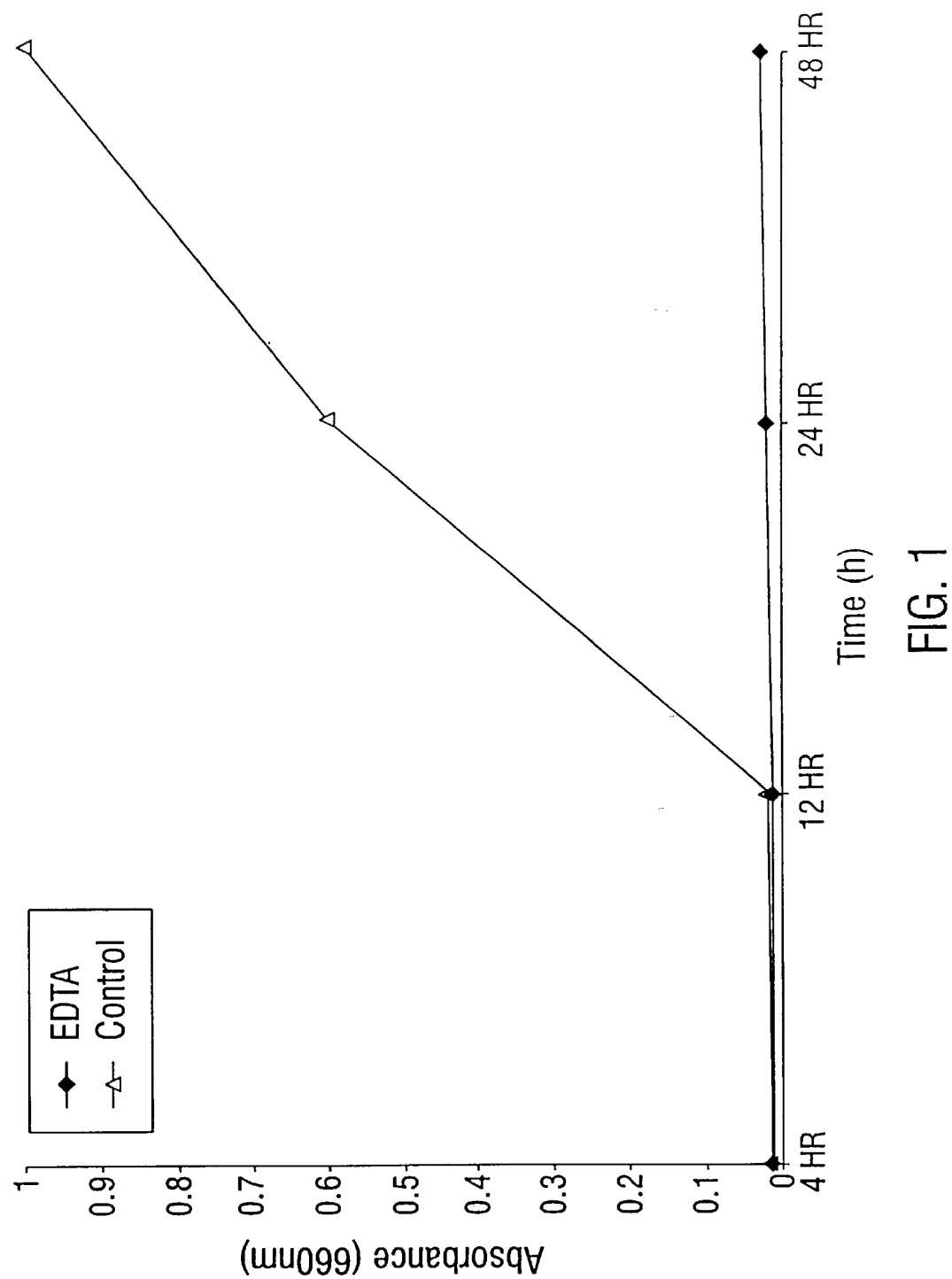
FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16 and FIG. 17 display plots of microbial population vs. time for cultures of species of Aspergillus, Candida, Fusarium, and certain bacteria. Response of these cultures to treatment with antimicrobials, chelators, and combinations thereof are indicated.

The present invention provides compositions and methods for the prevention and treatment of biofouling in water containing or submerged systems. The invention arises from the inventors' discovery that chelators have a significant growth inhibitory effect against species of fungal and bacterial microorganisms including Aspergillus, Fusarium, Candida, Pseudomonas, vancomycin-resistant enterococci, and multidrug resistant Stenotrophomonas (see data in FIG. 1, FIG. 2, FIG. 3, FIG. 4, FIG. 12, FIG. 13 and FIG. 14). Also, the inventors have demonstrated that, when combined with antifungal agents, chelators show additive to synergistic inhibitory activity against the growth of fungal microorganisms (see data in FIG. 5, FIG. 6, FIG. 7, FIG. 8, FIG. 9, FIG. 10 and FIG. 11). The inventors have further demonstrated that, when combined with antimicrobial compounds, chelators show additive to synergistic inhibitory activity against the growth of bacterial microorganisms (see data in FIG. 15, FIG. 16 and FIG. 17). These discoveries provide the basis for a novel program of prevention and treatment of microbial biofoulings using any of several embodiments of the inventive formulations, which may comprise various combinations of chelators, antifungal agents, antiseptic agents, antibacterial agents, and any necessary buffers, solvents, or surfactants.

All pipelines, including those which carry gas, oil, and water or other chemicals become contaminated with bacterial and fungal microorganisms. The same is true for commercial and industrial aqueous process and water handling systems. These microorganisms form biofilm on the surfaces of these pipelines and systems. This biofilm or slime comprises the glycocalyx of the microbial organisms contained therein. Most eukaryotic cells have a carbohydrate-rich zone about their periphery, and this peripheral zone or cell coat is made up of oligosaccharide side chains of glycolipids and integral membrane glycoproteins. Embedded in the biofilm environment, microorganisms such as bacteria and fungi benefit from a form of "extrinsic" resistance, thus rendering organisms which are ordinarily intrinsically and biologically sensitive to antimicrobials more resistant than they would otherwise be.

Colonies that include several kinds of bacteria and fungi can form deposits on metal surfaces, building slime layers and producing organic acids that cause pitting and accelerate corrosion of pipelines and associated metal structures. The inventors have shown that EDTA and other chelators of the present invention assist in disrupting and/or dissolving the glycocalyx of microbial colonies adherent to venous catheters. See, for example, U.S. Pat. No. 5,362,754 by Raad et al., or U.S. patent application Ser. No. 08/317,309 by Raad et al., both of which are herein incorporated by reference. The disruption and/or dissolution of microbial slime improves the activity of antimicrobial compounds against the bacteria, fungi, and other microbes embedded in the slime.

As used herein, and as standard in the art, a chelate is a type of coordination compound in which a central metal ion is attached by coordinate links to two or more nonmetal atoms in the same molecule. Heterocyclic rings are thus formed during chelation, with the metal atom as part of the ring. The molecule comprising the nonmetal linking atoms is termed a chelator. Chelators are used in various chemical applications, for example as titrating agents or as metal ion scavengers. Chelators can be used to remove ions from participation in biological reactions. For example, the well-known chelator ethylenediamine-N,N,N',N',-tetraacetic acid (EDTA) acts as an anticoagulant because it is capable of scavenging calcium ions from the blood.

It is known that iron and other trace metals are essential in the life cycle of microorganisms such as bacteria and fungi. Without these trace metals, microbes are unable to grow and reproduce. Although iron is abundant in nature, its availability for microbial assimilation is limited owing to the insolubility of ferric ions at neutral or alkaline pH. As a consequence, many microorganisms have evolved their own specialized trace metal-scavenging molecules, called siderophores, which bind with trace metals and make them available for uptake by bacteria and/or fungi. The chelators of the present invention have their inhibitory effect upon bacteria and fungi in part by virtue of competing with the microbial siderophores for any available trace metal ions. As noted above, the inventors have shown that EDTA and other chelators of the present invention assist in disrupting and/or dissolving the glycocalyx.

The inventors have discovered that chelators as described herein have significant growth inhibitory effect against many species of air- and water-borne microorganisms, including Aspergillus, Fusarium, Candida, Pseudomonas, vancomycin-resistant enterococci, and multidrug resistant Stenotrophomonas (see data in FIG. 1, FIG. 2, FIG. 3, FIG. 4, FIG. 12, FIG. 13 and FIG. 14). This is a significant discovery because, as noted in the Background section, cooling water systems used in power-generating plants, refineries, chemical plants, air conditioning systems and other commercial and industrial operations frequently encounter biofilm problems due to contamination from airborne organisms entrained by air/water contact in cooling towers, as well as waterborne organisms from the systems' makeup water supply.

Figure 2:
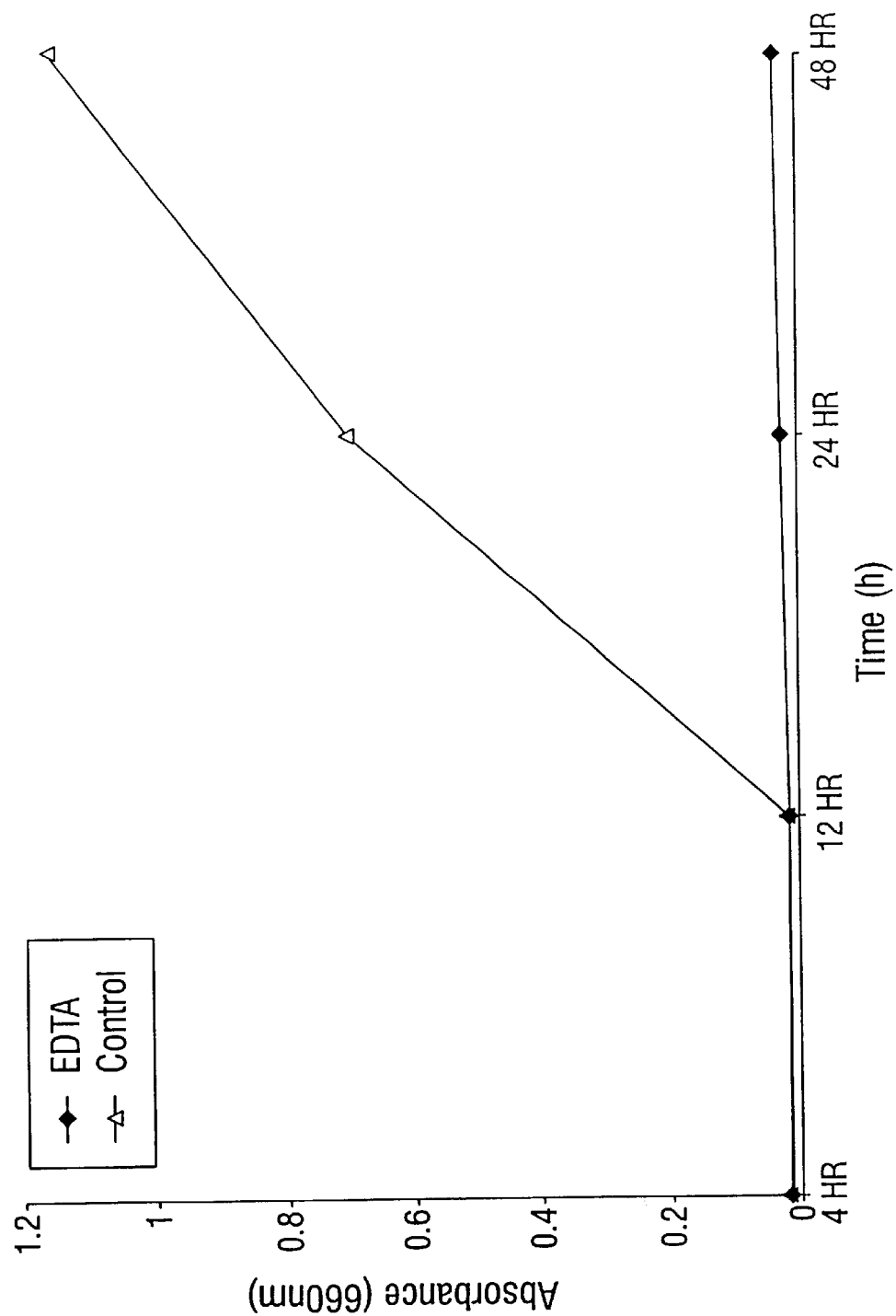
Figure 3:
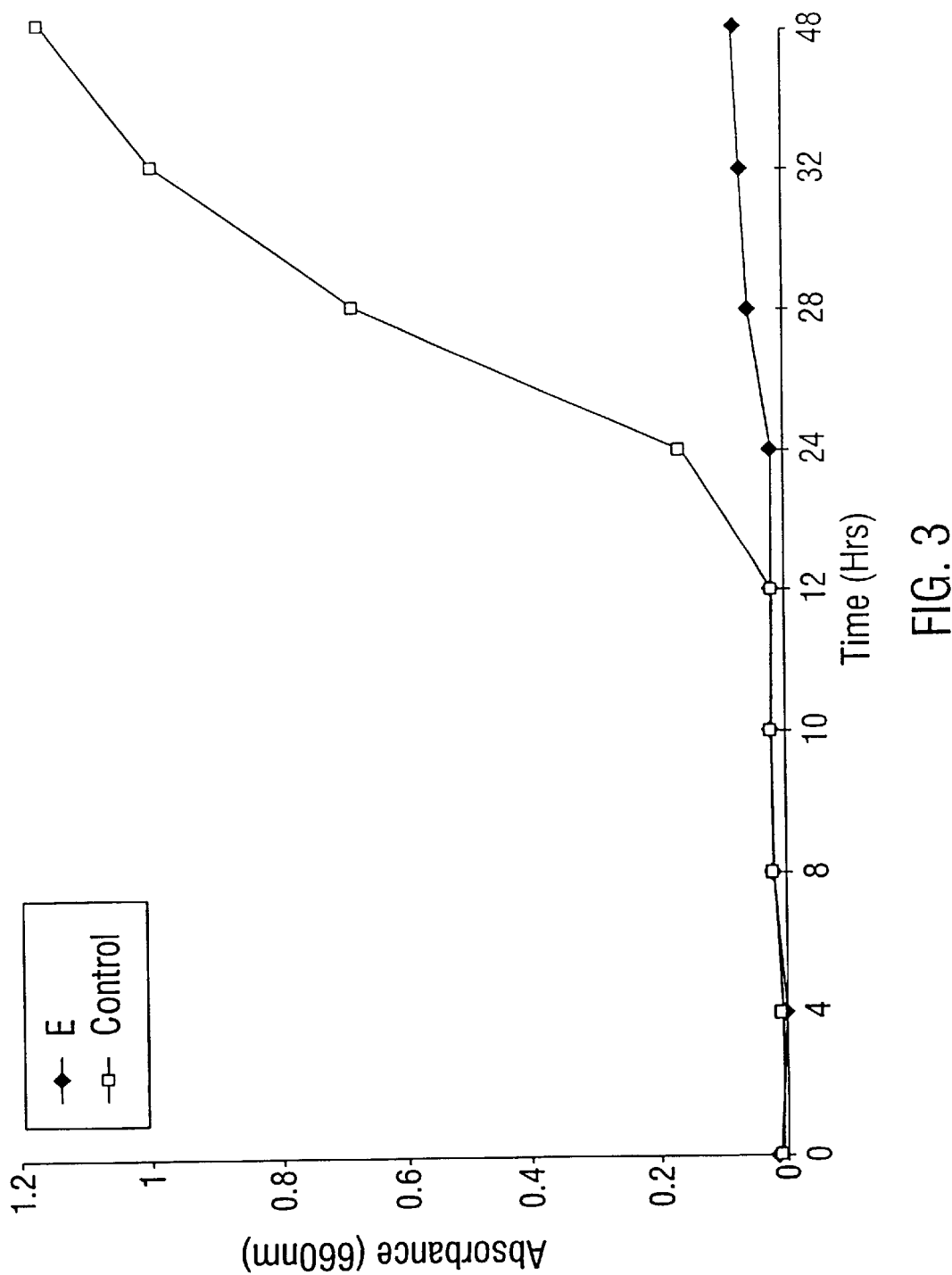
Figure 4:
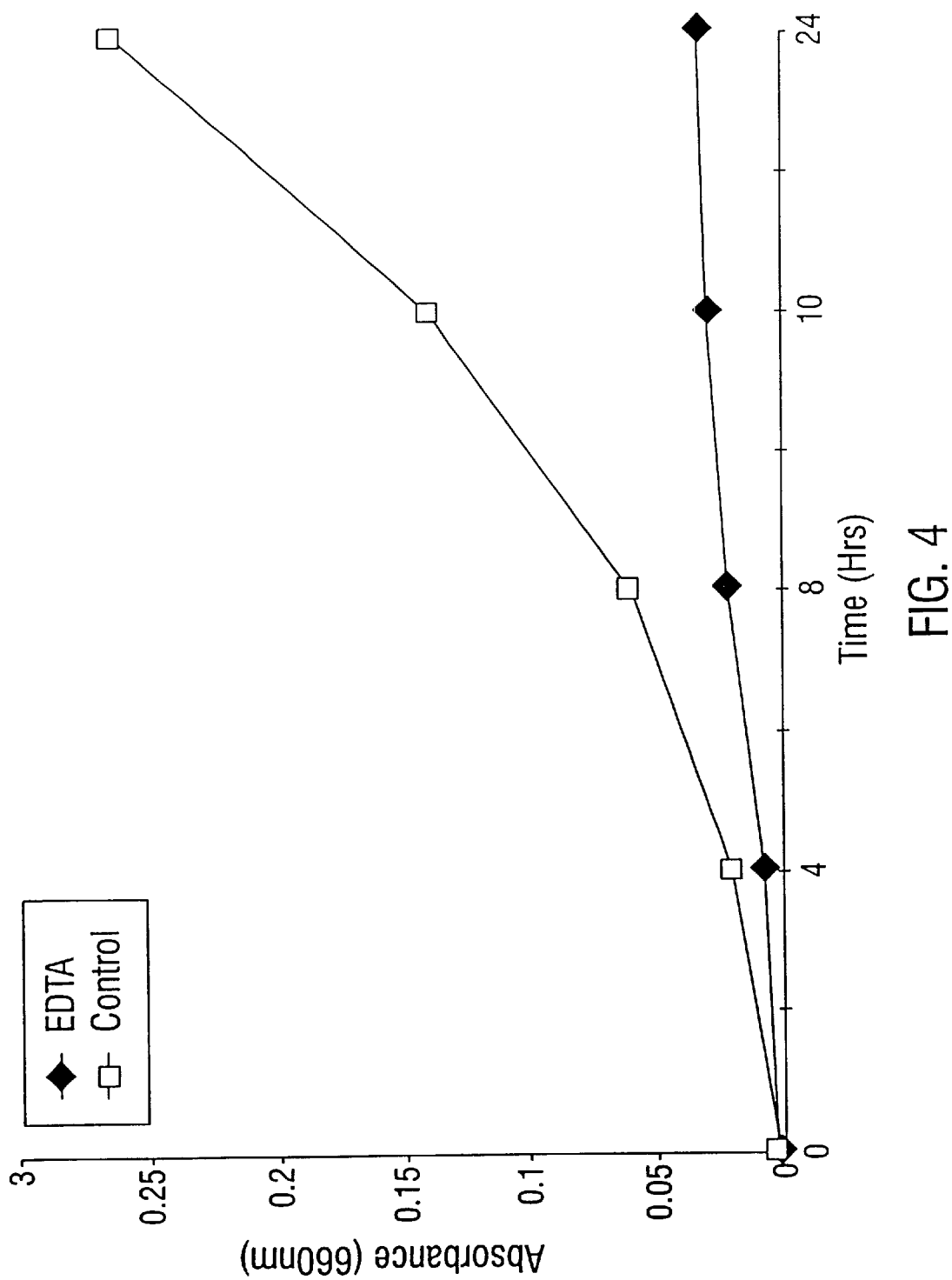
Figure 12:
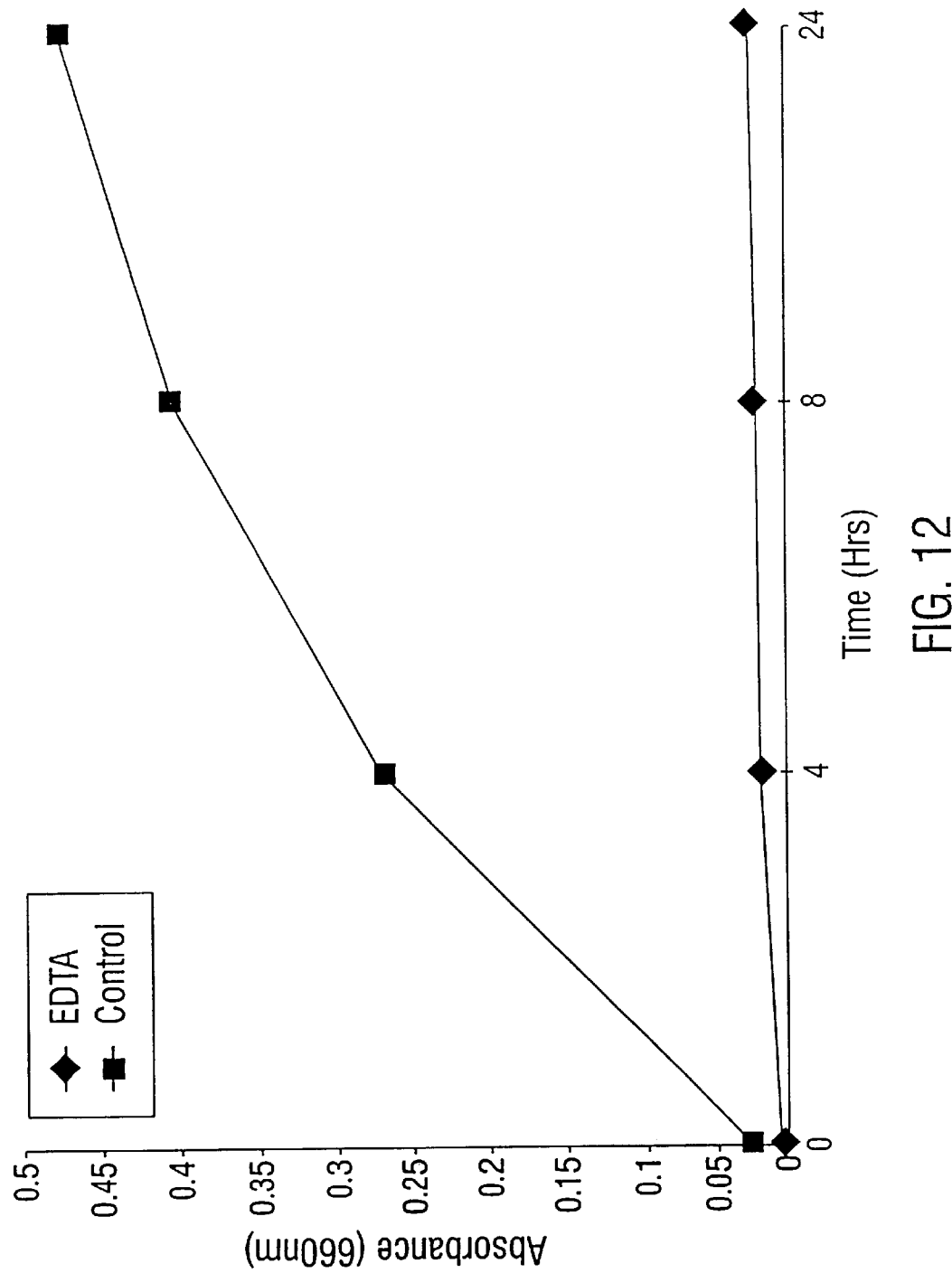
Figure 13:
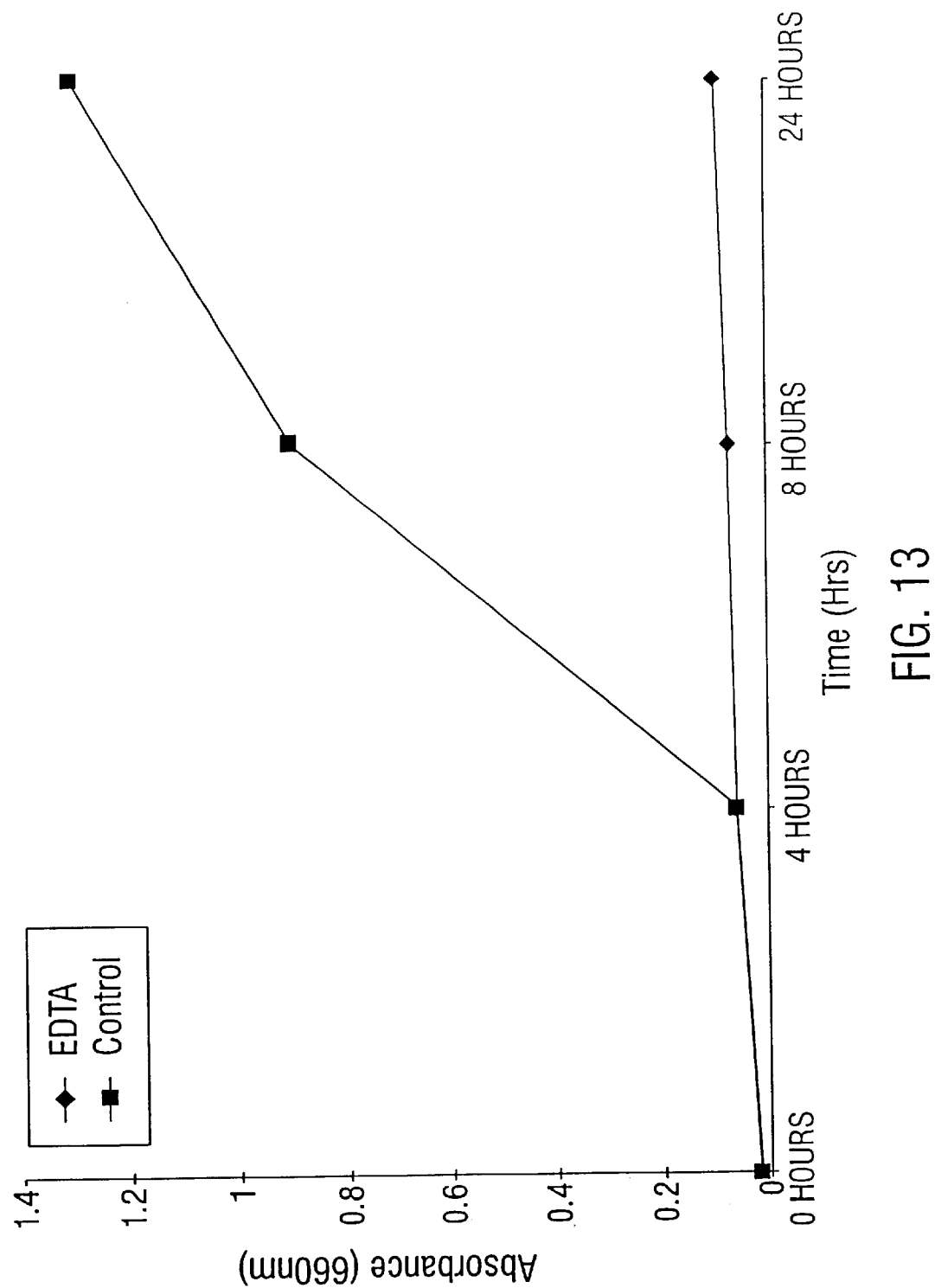
Figure 14:
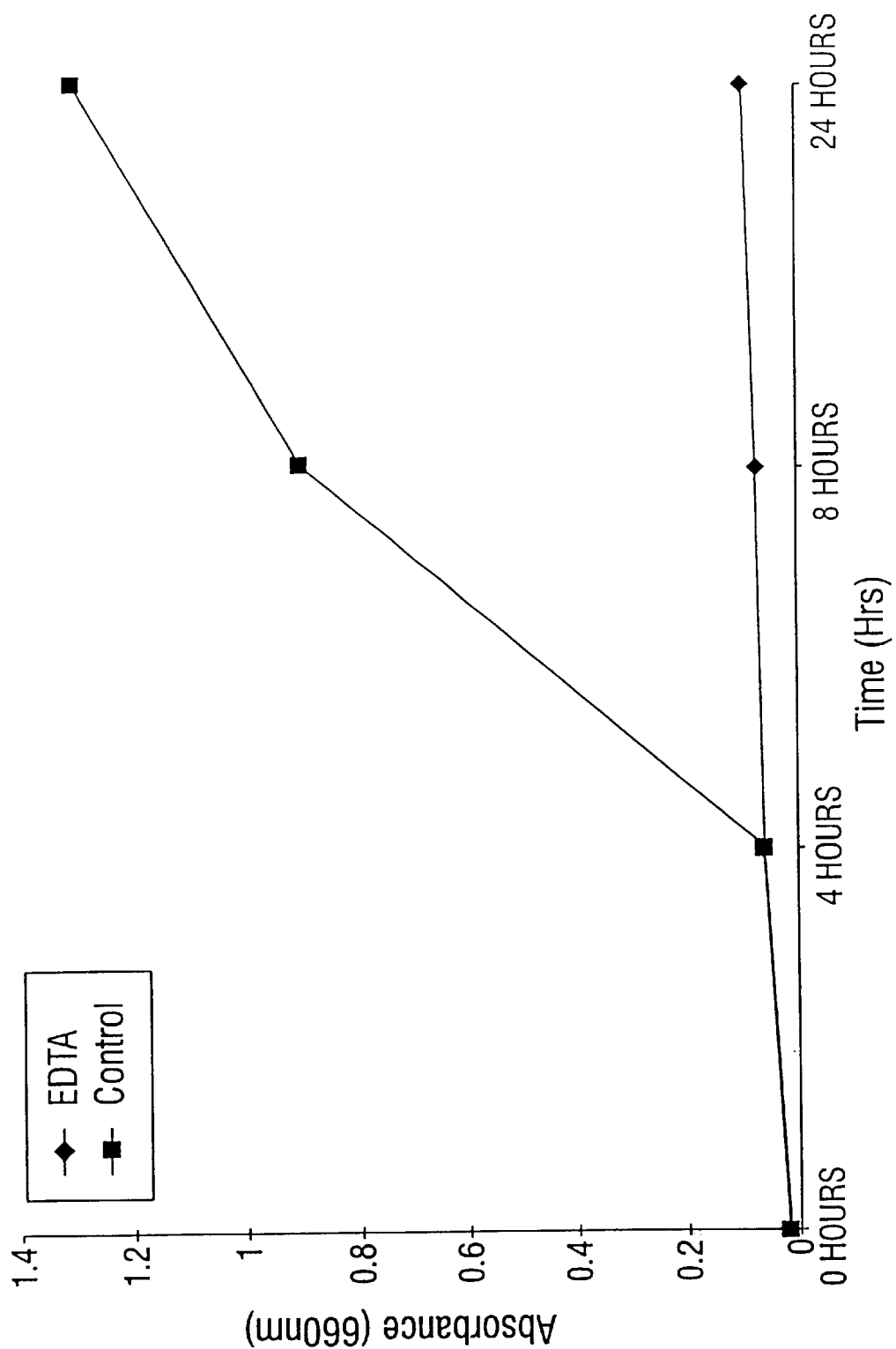

Referring to FIG. 1, it will be seen that EDTA exerts an inhibitory effect upon *Aspergillus flavus* relative to the control population. This effect is most clearly noticeable beginning 12 h after application of the chelator. Referring to FIG. 2 and FIG. 3, similar inhibitory behavior was noticed in cultures of *Aspergillus terreus* and multidrug resistant *Fusarium oxysporum* following application of EDTA. The inhibitory effect of EDTA on *Candida krusei* is noticeable only a few hours after contact of the fungus with the chelator, as shown in FIG. 4. As seen in FIG. 12, EDTA has a pronounced inhibitory effect upon multidrug resistant enterococcus. Referring to FIG. 13 and FIG. 14, it will be seen that EDTA exerts an inhibitory effect upon multidrug resistant *Stenotrophomonas maltophila* and likewise upon multidrug resistant Pseudomonas, relative to the control populations; in both cases, this inhibitory effect is most clearly noticeable beginning approximately 4 h after application of the chelator. Experimental conditions for the inhibition studies described in FIG. 1, FIG. 2, FIG. 3, FIG. 4, FIG. 12, FIG. 13, and FIG. 14 may be found under Example 1 below.

Table 1 provides a representative list of chelators useful in conjunction with the present invention. Preferred chelators are those which bind trace metal ions with a binding constant ranging from about $10^1$ to about $10^{100}$; more preferred chelators are those which bind trace metal ions with a binding constant ranging from about $10^{10}$ to about $10^{80}$; most preferred chelators are those which bind trace metal ions with a binding constant ranging from about $10^{15}$ to about $10^{60}$.

TABLE 1

CHELATORS

| ABBREVIATION | FULL NAME |
| --- | --- |
| EDTA free acid | Ethylenediamine-N,N,N',N',-tetraacetic acid |
| EDTA 2Na | Ethylenediamine-N,N,N',N',-tetraacetic acid, disodium salt, dihydrate |
| EDTA 3Na | Ethylenediamine-N,N,N',N',-tetraacetic acid, trisodium salt, trihydrate |
| EDTA 4Na | Ethylenediamine-N,N,N',N'-tetraacetic acid, tetrasodium salt, tetrahydrate |
| EDTA 2K | Ethylenediamine-N,N,N',N'-tetraacetic acid, dipotassium salt, dihydrate |
| EDTA 2Li | Ethylenediamine-N,N,N',N'-tetraacetic acid, dilithium salt, monohydrate |
| EDTA 2NH4 | Ethylenediamine-N,N,N',N'-tetraacetic acid, diammonium salt |
| EDTA 3K | Ethylenediamine-N,N,N',N'-tetraacetic acid, tripotassium salt, dihydrate |
| Ba(II)-EDTA | Ethylenediamine-N,N,N',N'-tetraacetic acid, barium chelate |
| Ca(II)-EDTA | Ethylenediamine-N,N,N',N'-tetraacetic acid, calcium chelate |
| Ce(III)-EDTA | Ethylenediamine-N,N,N',N'-tetraacetic acid, cerium chelate |
| Co(II)-EDTA | Ethylenediamine-N,N,N',N'-tetraacetic acid, cobalt chelate |
| Cu(II)-EDTA | Ethylenediamine-N,N,N',N'-tetraacetic acid, copper chelate |

TABLE 1-continued

CHELATORS

| ABBREVIATION | FULL NAME |
|---|---|
| Dy(III)-EDTA | Ethylenediamine-N,N,N',N'-tetraacetic acid, dysprosium chelate |
| Eu(III)-EDTA | Ethylenediamine-N,N,N',N'-tetraacetic acid, europium chelate |
| Fe(III)-EDTA | Ethylenediamine-N,N,N',N'-tetraacetic acid, iron chelate |
| In(III)-EDTA | Ethylenediamine-N,N,N',N'-tetraacetic acid, indium chelate |
| La(III)-EDTA | Ethylenediamine-N,N,N',N'-tetraacetic acid, lanthanum chelate |
| Mg(II)-EDTA | Ethylenediamine-N,N,N',N'-tetraacetic acid, magnesium chelate |
| Mn(II)-EDTA | Ethylenediamine-N,N,N',N'-tetraacetic acid, manganese chelate |
| Ni(II)-EDTA | Ethylenediamine-N,N,N',N'-tetraacetic acid, nickel chelate |
| Sm(III)-EDTA | Ethylenediamine-N,N,N',N'-tetraacetic acid, samarium chelate |
| Sr(II)-EDTA | Ethylenediamine-N,N,N',N'-tetraacetic acid, strontium chelate |
| Zn(II)-EDTA | Ethylenediamine-N,N,N',N'-tetraacetic acid, zinc chelate |
| CyDTA | trans-1,2-Diaminocyclohexane-N,N,N',N'-tetraaceticacid, monohydrate |
| DHEG | N,N-Bis(2-hydroxyethyl)glycine |
| DTPA-OH | 1,3-Diamino-2-hydroxypropane-N,N,N',N'-tetraacetic acid |
| DTPA | 1,3-Diaminopropane-N,N,N',N'-tetraacetic acid |
| EDDA | Ethylenediamine-N,N'-diacetic acid |
| EDDP | Ethylenediamine-N,N'-dipropionic acid dihydrochloride |
| EDDPO | Ethylenediamine-N,N'-bis(methylenephosphonic acid), hemihydrate |
| EDTA-OH | N-(2-Hydroxyethyl)ethylenediamine-N,N',N'-triacetic acid |
| EDTPO | Ethylenediamine-N,N,N',N'-tetrakis(methylenephosponic acid) |
| EGTA | O,O'-bis(2-aminoethyl)ethyleneglycol-N,N,N',N'-tetraacetic acid |
| HBED | N,N-bis(2-hydroxybenzyl)ethylenediamine-N,N-diacetic acid |
| HDTA | 1,6-Hexamethylenediamine-N,N,N',N'-tetraacetic acid |
| HIDA | N-(2-Hydroxyethyl)iminodiacetic acid |
| IDA | Iminodiacetic acid |
| Methyl-EDTA | 1,2-Diaminopropane-N,N,N',N'-tetraacetic acid |
| NTA | Nitrilotriacetic acid |
| NTP | Nitrilotripropionic acid |
| NTPO | Nitrilotris(methylenephosphoric acid), trisodium salt |
| O-Bistren | 7,19,30-Trioxa-1,4,10,13,16,22,27,33-octaazabicyclo [11,11,11] pentatriacontane, hexahydrobromide |
| TTHA | Triethylenetetramine-N,N,N',N'',N''',N'''-hexaacetic acid |

The classes of compounds known currently to act as antifungal agents, and which are contemplated to be useful in the practice of the present invention include, but are not limited to, the polyenes, the imidazoles and triazoles, griseofulvin, and flucytosine. The polyenes bind to ergosterols in fungal membranes, resulting in the formation of transmembrane channels which allow the escape of metabolites essential to maintaining the viability of the fungal cell. The imidazoles and triazoles are structurally related and share the same antifungal spectrum and mechanism of action, namely the inhibition of the fungal sterol 14-α-demethylase enzyme system. Griseofulvin was isolated from a species of Penicillium and acts by inhibiting fungal mitosis. Flucytosine is a fluorinated pyrimidine which acts upon fungi by inhibiting thymidylate synthetase.

The inventors have demonstrated that Amphotericin B acts synergistically in concert with the chelator EDTA to inhibit many species of air- and water-borne microorganisms, including Aspergillus, Fusarium, vancomycin-resistant enterococci, and multidrug resistant Stenotrophomonas (a drug combination is said to exhibit synergism when the combination achieves a desired effect one order of magnitude or greater than the analogous effect of the most potent individual constituent of the combination) See data in FIG. 5, FIG. 6, FIG. 7, FIG. 8, FIG. 9, FIG. 10, FIG. 11, FIG. 15, FIG. 16 and FIG. 17. This is significant because, as noted in the Background section, cooling water systems used in power-generating plants, refineries, chemical plants, air conditioning systems and other commercial and industrial operations frequently encounter biofilm problems due to contamination from airborne organisms entrained by air/water contact in cooling towers, as well as waterborne organisms from the systems' makeup water supply.

Figure 5:
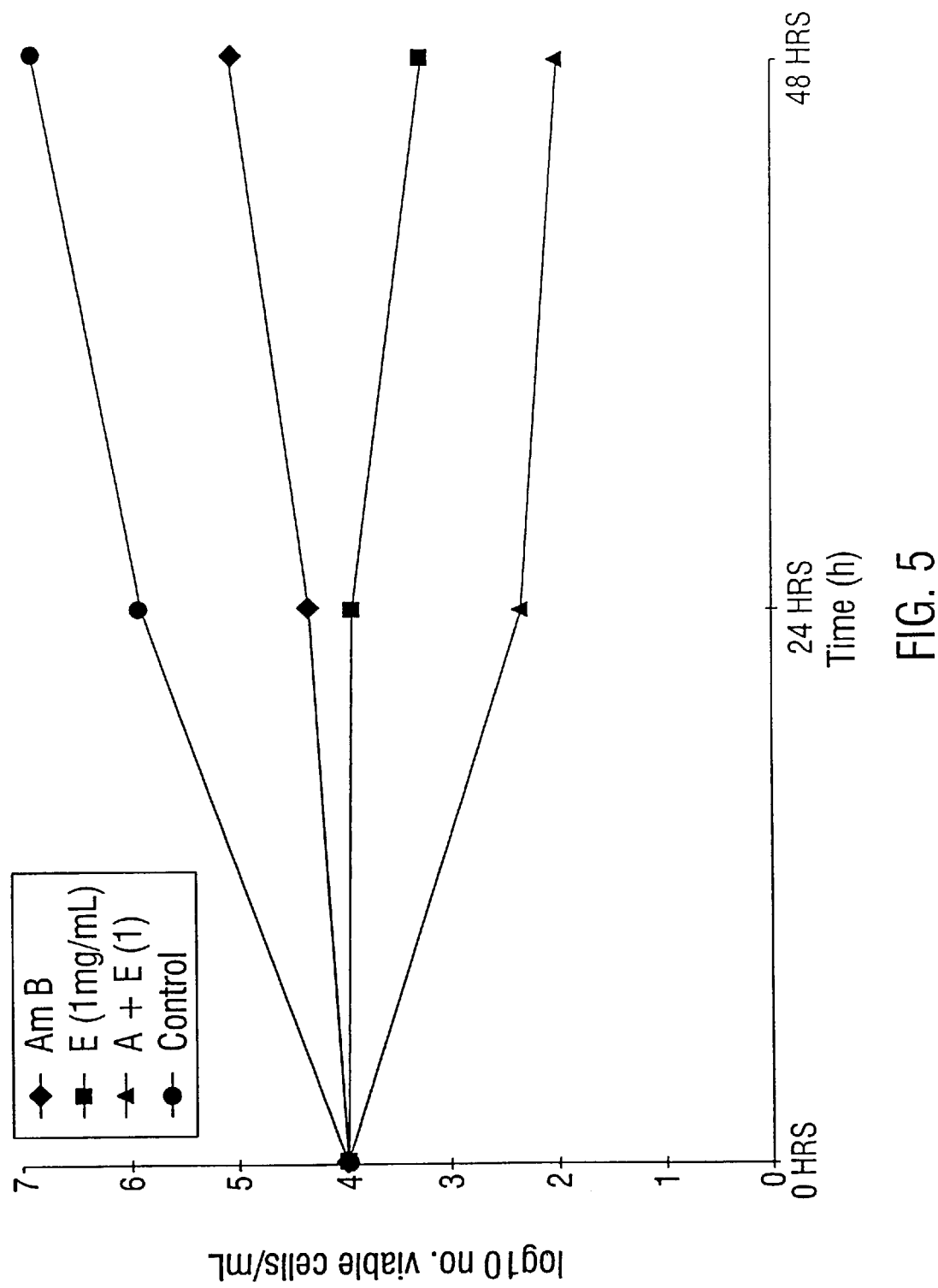
Figure 6:
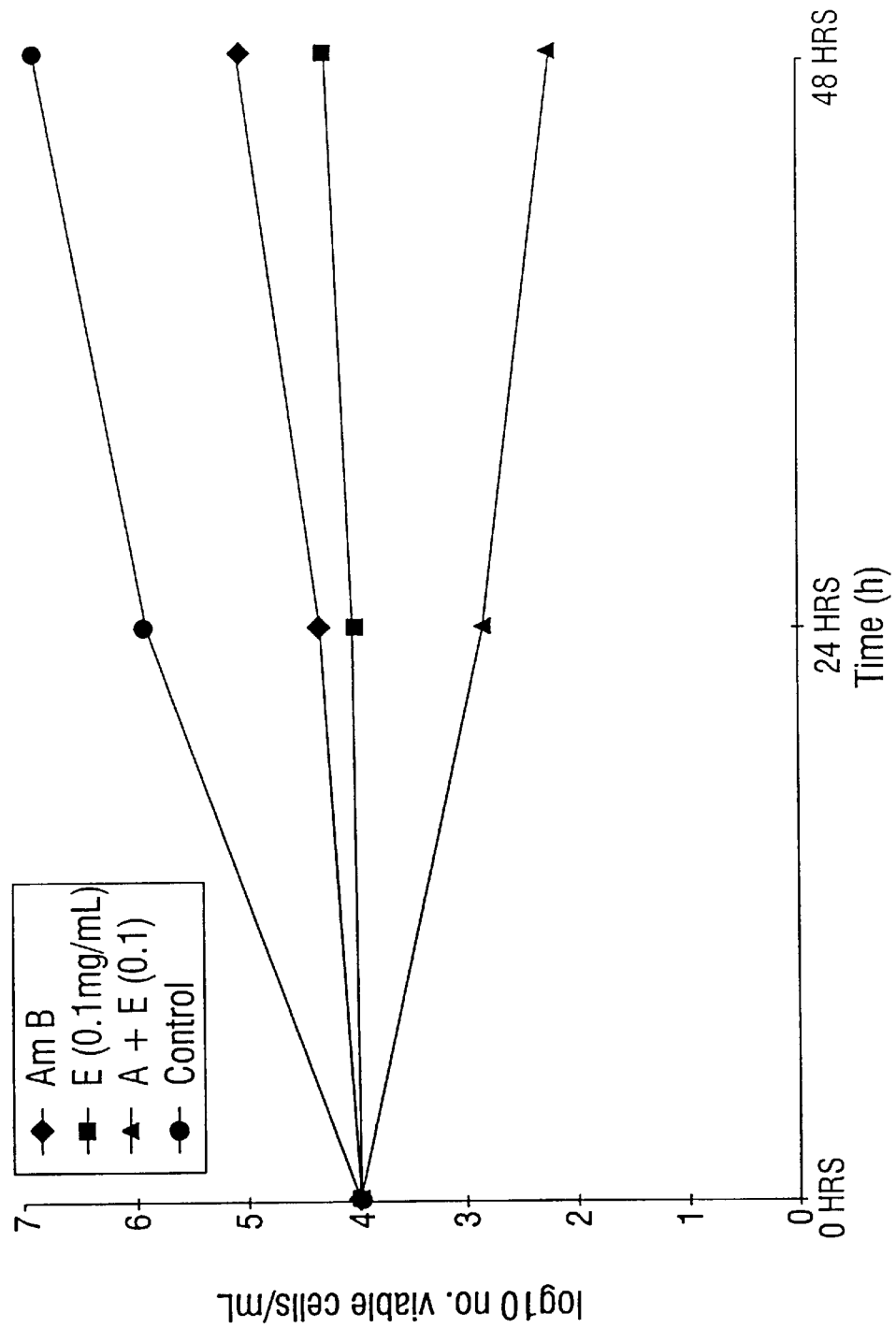
Figure 7:
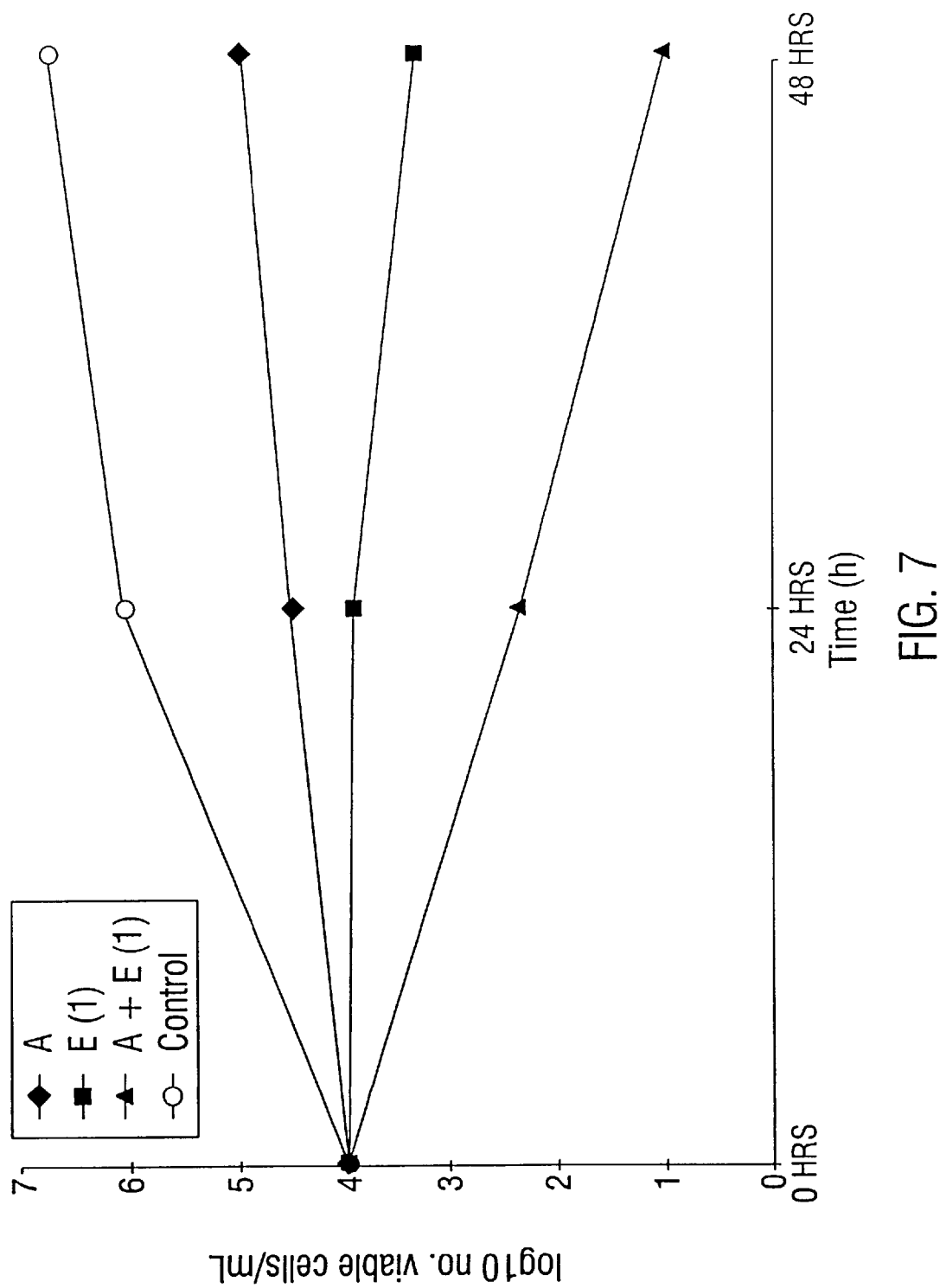
Figure 8:
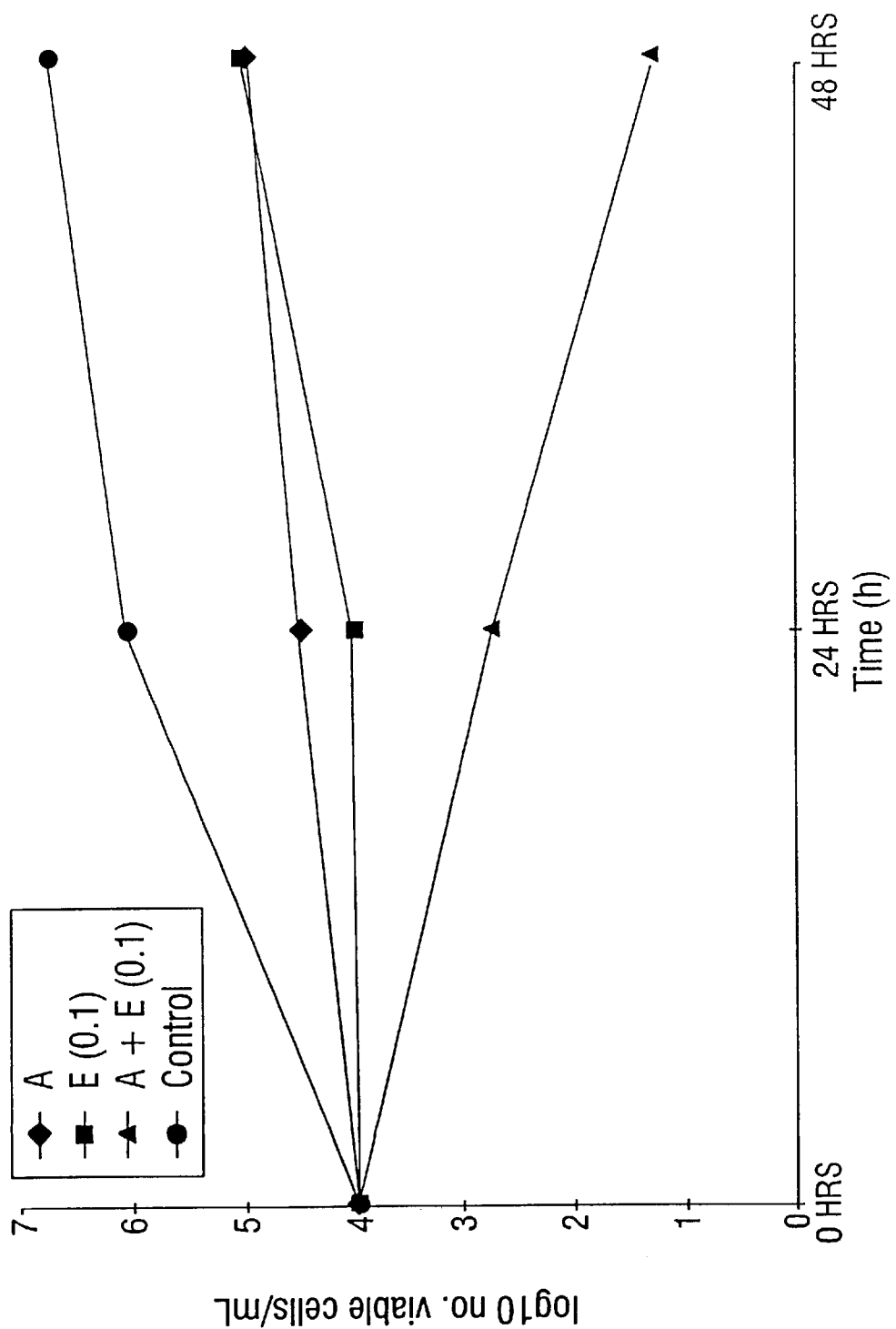
Figure 9:
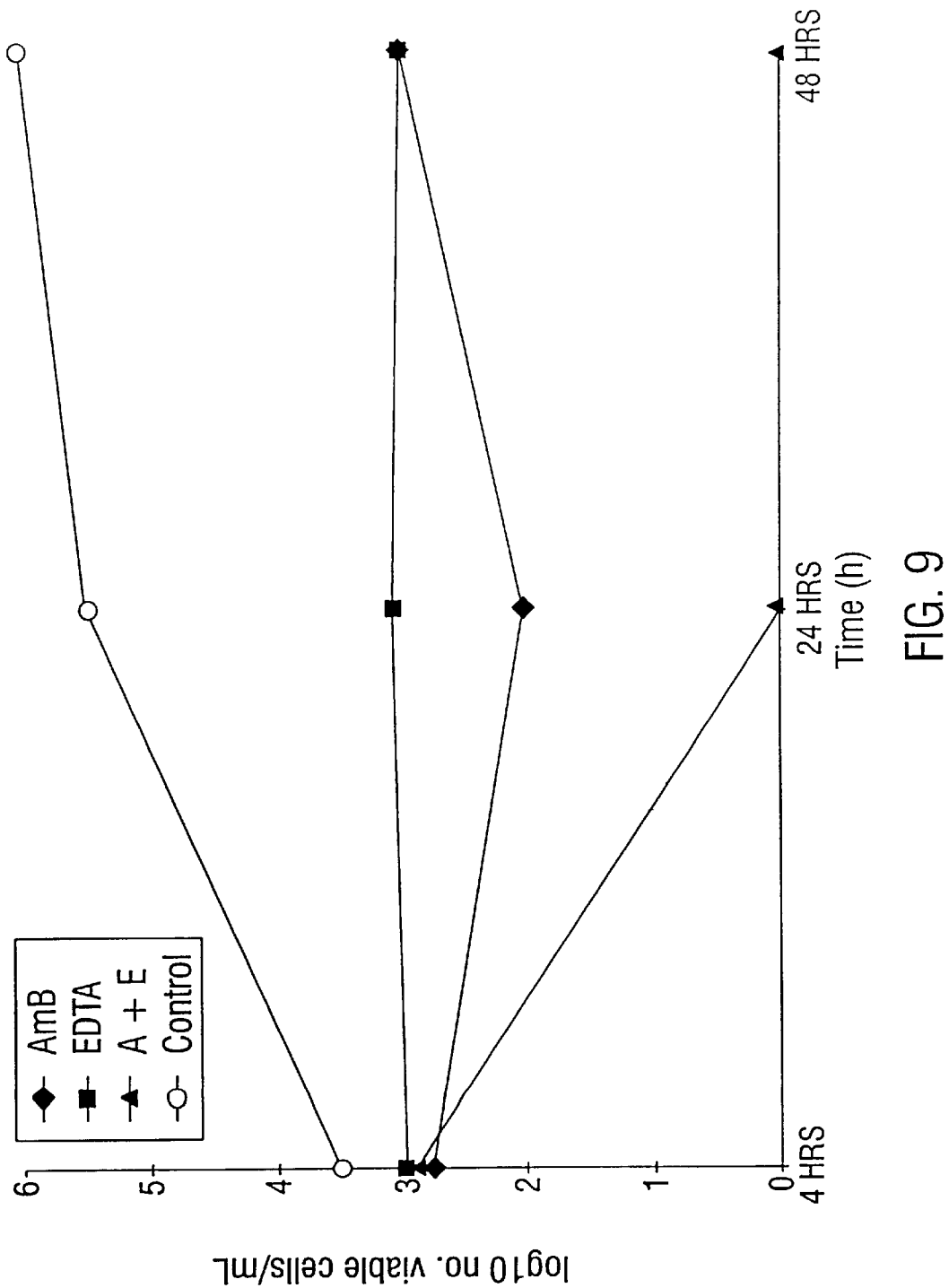
Figure 10:
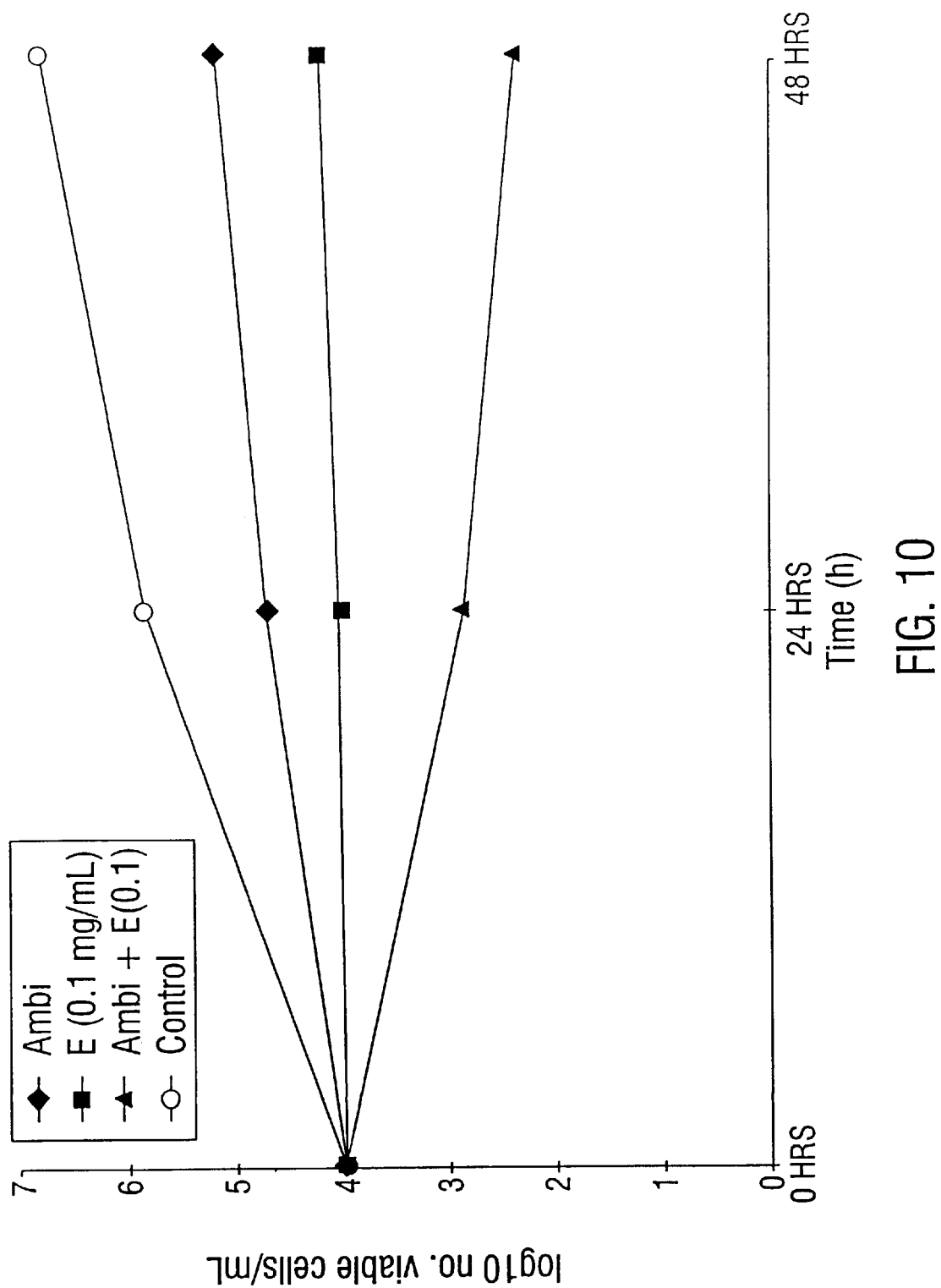
Figure 11:
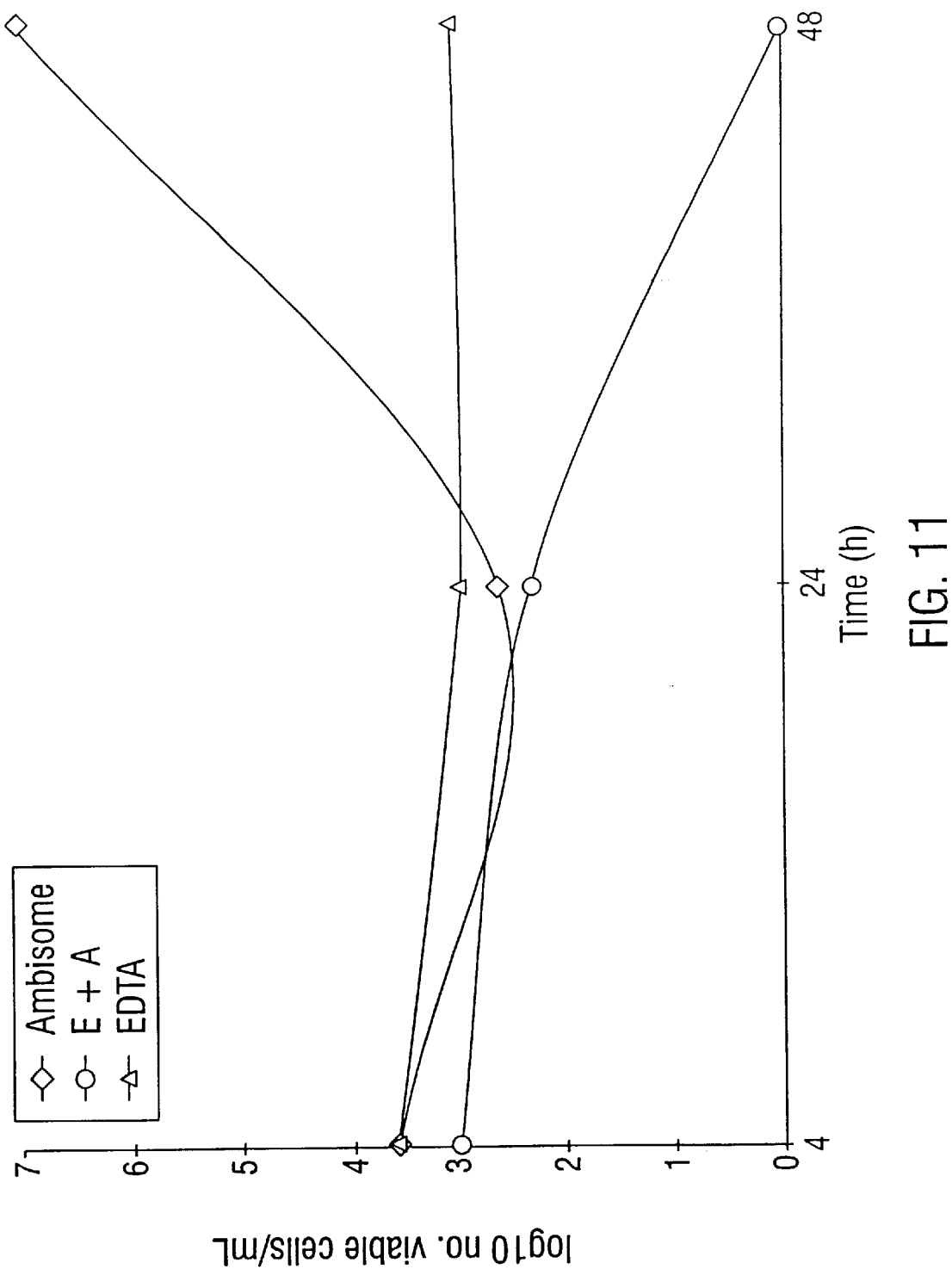
Figure 15:
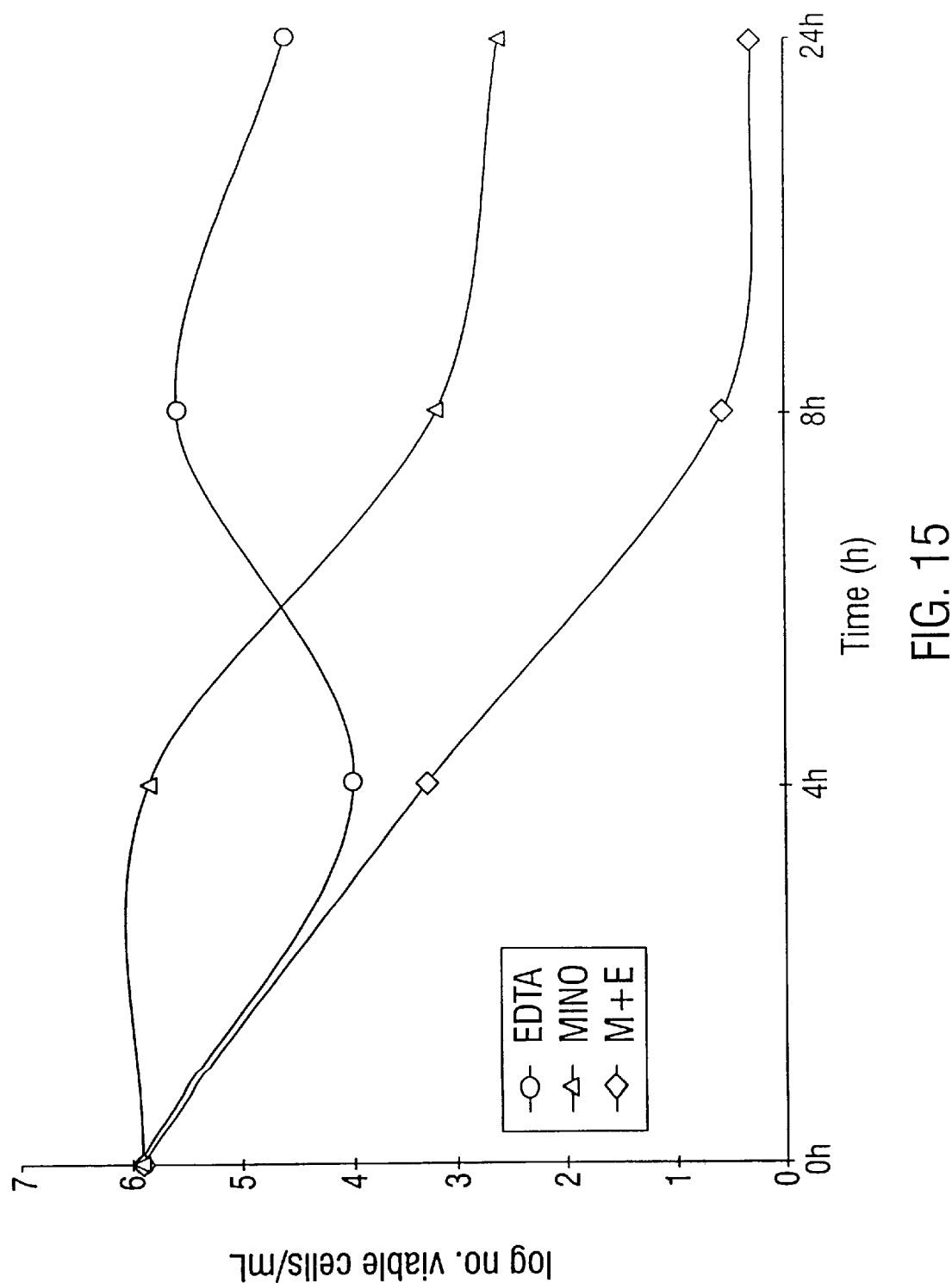
Figure 16:
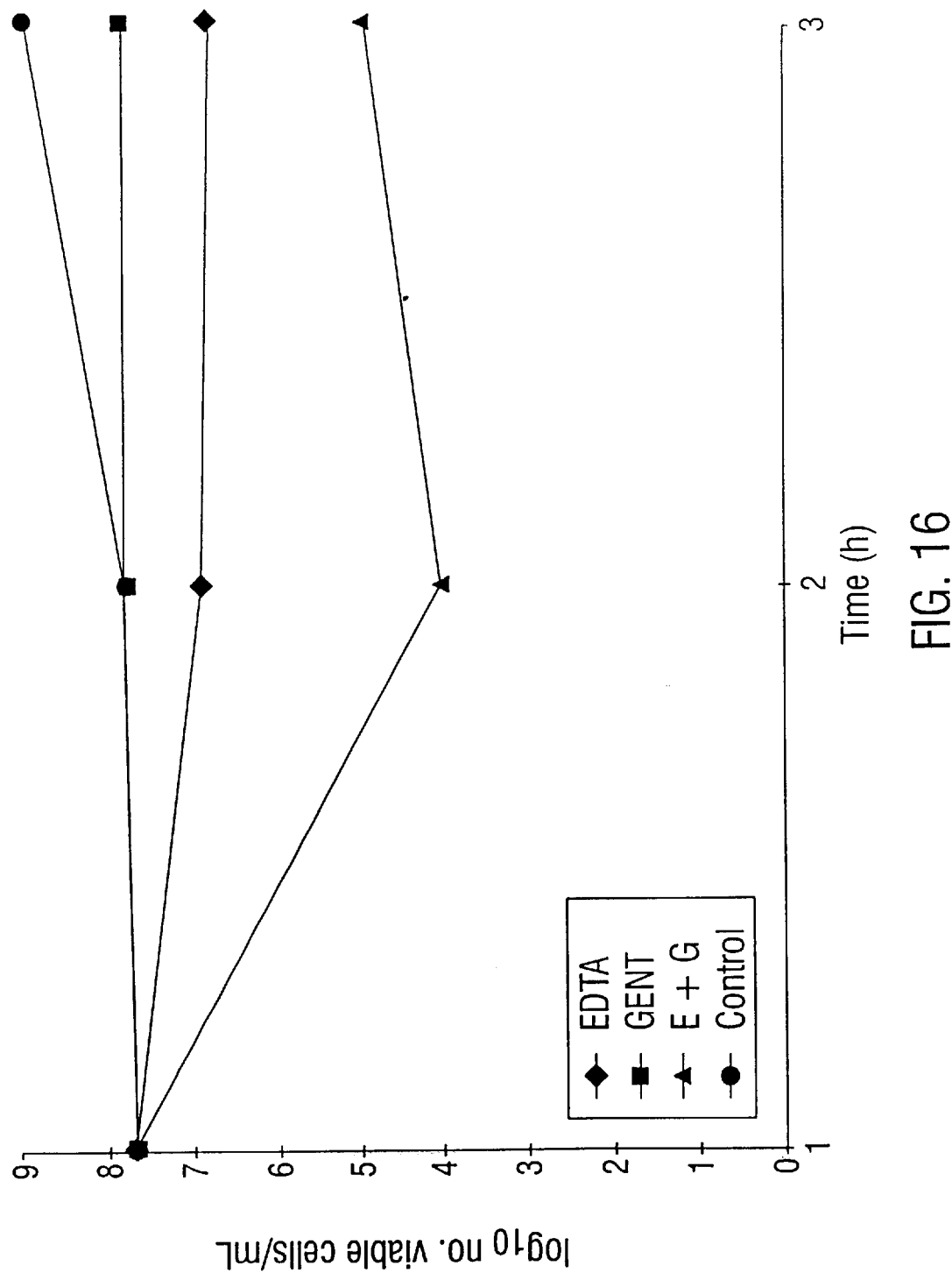
Figure 17:
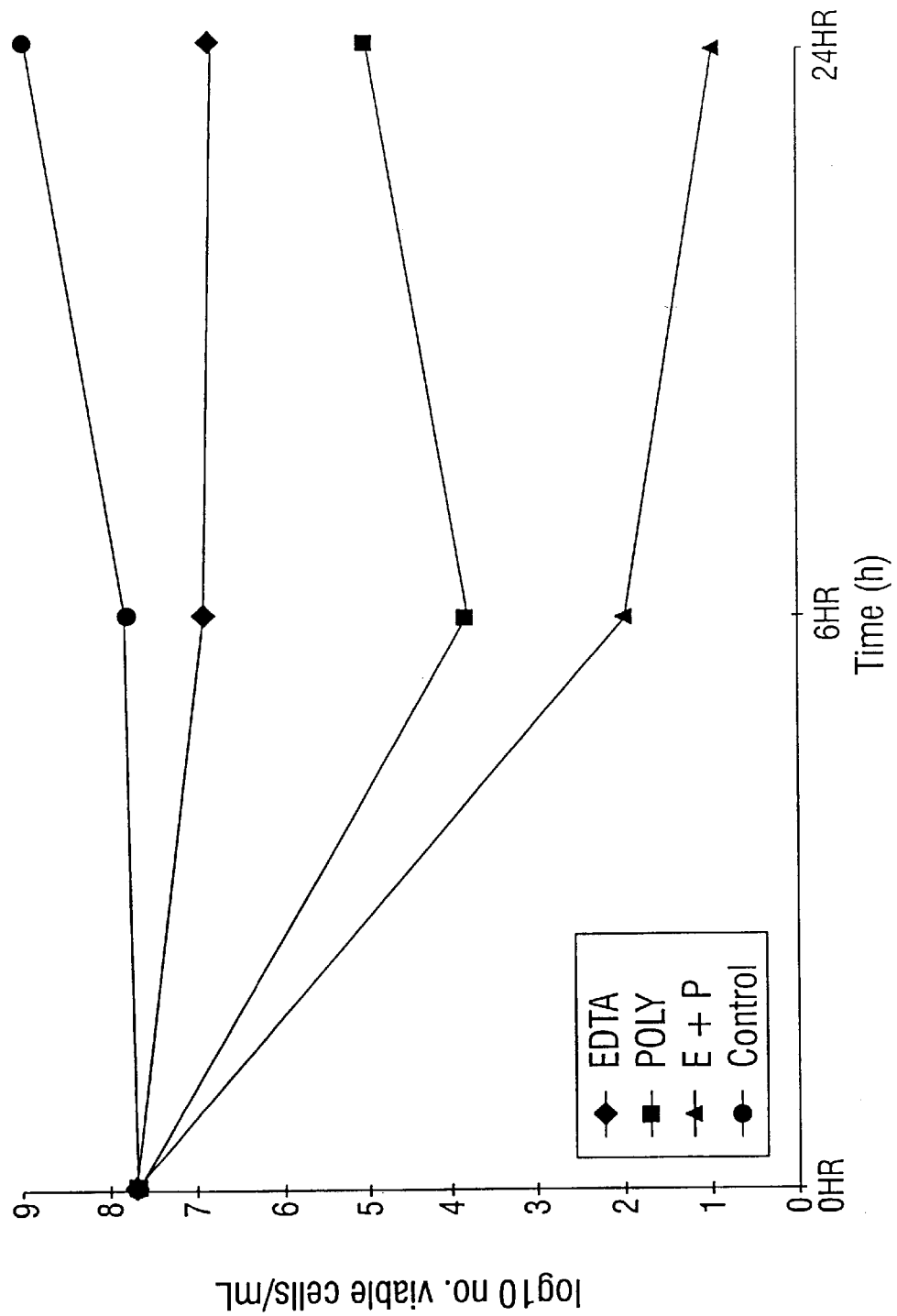

Referring to FIG. 5, Amphotericin B at a concentration of 1 μg/mL and EDTA at a concentration of 1 mg/mL act synergistically to inhibit the growth of *Aspergillus fumigatus* by a margin of almost two orders of magnitude relative to EDTA acting alone. The same effect is observed when the concentration of EDTA is reduced to 0.1 mg/mL (FIG. 6). Likewise, Amphotericin B and EDTA inhibit *Aspergillus flavus* synergistically, whether EDTA is present at 1.0 mg/mL or 0.1 mg/mL (FIG. 7 and FIG. 8). This synergy extends to inhibition of *Fusarium solani* as well, as seen in FIG. 9. In FIG. 10 and FIG. 11 the inhibitory effect of liposomal Amphotericin B and EDTA against *A. fumigatus* and *F. solani*, respectively, is demonstrated. In FIG. 15, the inhibitory effect of minocycline and EDTA against vancomycin-resistant enterococci is shown. FIG. 16 shows the synergistic inhibition of *S. maltophilia* by gentamycin and EDTA, and FIG. 17 shows the synergistic inhibition of *S. maltophilia* by polymyxin B and EDTA. Experimental conditions for the synergy studies described in FIG. 5, FIG. 6, FIG. 7, FIG. 8, FIG. 9, FIG. 10, FIG. 11, FIG. 15, FIG. 16 and FIG. 17 may be found under Examples 2, 3 and 4 below.

Antifungal agents particularly preferred in connection with the present invention include the polyenes, most preferably Amphotericin B and all soluble forms of Amphotericin B, i.e. liposomal complexes, suspensions, and the like. Table 2 provides a representative list of antifungal agents useful in conjunction with the present invention. The list in Table 2 is not meant to be exhaustive.

TABLE 2

ANTIFUNGALS

| | |
|---|---|
| UK 109,496 (Voriconazole) | Terbinafine |
| SCH 56592 | BF-796 |
| ER30346 | MTCH 24 |
| UK 9746 | BTG-137586 |
| UK 9751 | RMP-7/Amphotericin B |
| T 8581 | Omoconazole |
| Flutrimazole | Amphotericin B |
| Cilofungin LY121019 | Nystatin |
| LY303366 (Echinocandin) | Natamycin |
| L-743872 (Pneumocandin) | Clotrimazole |
| Pradimicins (MNS 18184) | Miconazole |
| Benanomicin | Ketoconazole |
| Ambisome | Terconazole |
| ABLC | Econazole |
| Liposomal Amphotericin | Itraconazole |
| ABCD | Fluconazole |
| Liposomal Nystatin | Griseofulvin |
| Nikkomycin Z | Flucytosine |

In addition, the present invention may be used in conjunction with or may alternate with known biofouling treatments. Such treatments may include, but are not limited to, non-oxidizing biocides such as isothiazolones, formaldehyde and glutaraldehyde. Other concurrent treatments may include the addition of acidic or alkaline compounds to control the pH level, or addition of oxidizing biocides to the water, such as chlorine, chlorine dioxide, chlorine donors, and ozone. Other sanitizing agents and systems which are known in the art may also be used with the methods and compositions of the present invention. For example, 0.1–1.0 parts per million (ppm) of copper and/or silver ions, 2–12 ppm alkyl, dialkyl, or polymeric quaternary ammonium compounds, or 6–10 ppm poly(hexamethylene biguanide), commonly referred to as PHMB are all treatments standard in the art which may be used in conjunction with the practice of the present invention.

In U.S. Pat. No. 5,449,658, Unhoch et al. describe the addition of a "potentiating adjuvant," ethylenediamine tetraacetic acid (EDTA), to PHMB in amounts sufficient to render the antimicrobial composition algicidal and fungicidal in water, followed by the use of a peroxy salt as a "backup agent" to discourage regrowth of microorganisms in the aqueous system being treated. Unhoch et al. recognized that at its usual dosages of 6–10 ppm, PHMB is bactericidal, but generally only algistatic and fungistatic. To improve the killing levels of PHMB against algae and fungi, the chelator EDTA is introduced at a dosage of 1.5–36 ppm, thus improving the efficacy of PHMB. However, Unhoch et al. failed to recognize that chelators can, by themselves, have an inhibitory effect against certain airborne and waterborne microorganisms. This is evidenced by their statement that "EDTA has been used as a chelating agent in swimming pools and spas to chelate metals such as iron to prevent staining or scale formation . . . EDTA has no fungicidal or algicidal activity of its own . . . and has not been used as an algistat or fungistat in swimming pools, spas, or the like." By contrast, the chelators of the present invention have been demonstrated to have a distinct inhibitory effect, acting either alone or in concert with antimicrobial agents, upon several well-known species of bacteria and fungi. Further, Unhoch et al. have not shown, as have the present inventors, that chelators such as those of the present invention may combine with antimicrobial agents such as those of the present invention to produce a synergistic inhibitory effect up on a wide spectrum of the slime-producing microorganisms which cause biofouling in commercial and industrial water systems.

The methods disclosed herein may be further enhanced by treating the water with a backup agent comprising a peroxy salt (a salt which produces hydrogen peroxide in water), such as a percarbonate, peracetate, persulfate, peroxide, or perborate, but preferably with an alkali metal perborate, in a manner similar to that described in U.S. Pat. No. 4,253,971, which is incorporated herein by reference. For example, after an initial treatment of the water with a chelator/antimicrobial composition according to the present invention, the water may be further treated by adding a sodium perborate salt to the water at the rate of about 1 to 36 ppm per week, preferably about 12 to 24 ppm per week as a backup. Additionally, the method and apparatus for ozonolysis of aqueous systems disclosed in U.S. Pat. No. 5,591,349, incorporated herein by reference, may be used in conjunction with the compositions and methods of the present invention. For example, the method of treatment of the present invention could be alternated with the ozonolysis method to ensure effective, broad-spectrum killing of slime-producing microorganisms.

With benefit of the present disclosure, one of skill in the art will recognize that the compositions and methods of the present invention may be used in conjunction with any of the abrasive cleaning technologies known in the art. For example, U.S. Pat. No. 5,615,696 discloses a rotating, cleaning nozzle(s) which emits high pressure water or other fluids for cleaning the surfaces of a pipeline. The pressure of the water is established to effectively remove the coating or other material on the pipeline without damaging the substrate or pipe. Thus, the speed of the longitudinal movement of the cleaning apparatus along the pipeline, together with the rotational or linear speed of the rotating water jet, must also be determined in order to provide the most effective cleaning action without damage to the pipe. Thus, rotary seals associated with the rotating nozzles or swivel heads are subjected to vibrations and wear from the high pressures and speeds involved which results in a short life thereby requiring costly replacements. One of the key features of the disclosed apparatus is provision of a nozzle capable of sweeping over a broad area using a system operating at pressure over 30,000 pounds per square inch (psi). This system covers a wide area with a nozzle moving over the area. Nozzle movement, even rotating movement is accomplished by a piped system which does not have any high pressure seals in it. The nozzle movement is accommodated by a flexible hose connection to a moving nozzle with no seals to fail. One of skill in the art will recognize that the compositions of the present invention are ideal for use with such a rotating cleaning nozzle.

Similarly, the compositions of the present invention may be used with the water-driven turbine/brush assembly disclosed in U.S. Pat. No. 5,406,666, incorporated herein by reference. A first embodiment includes an assembly comprising a small turbine with angled blades axially mounted between inner and outer rings, on one end of a standoff support. An O-ring for stabilizing the assembly within the pipe is mounted in a groove within the outer ring. A replaceable circular brush is fixedly mounted on the opposite end of the standoff support and can be used for cleaning robes and pipes of various diameters, lengths and configurations. The turbine, standoff support, and brash spin in unison relative to a hub bearing that is fixedly attached to a wire upstream of the assembly. The nonrotating wire is for retaining the assembly in tension and enabling return of the assembly to the pipe entrance. The assembly is initially placed in the pipe or tube to be cleaned. A pressurized water or solution source is provided at a required flow-rate to propel the assembly through the pipe or tube. The upstream water pressure propels and spins the turbine, standoff support and brush. The rotating brush combined with the solution cleans the inside of the pipe. The solution flows out of the other end of the pipe with the brush rotation controlled by the flow-ram. One of skill in the art will recognize that the compositions of the present invention are ideal for use with such a water-driven turbine/brush assembly, such as by including the compositions of the present invention in the solutions of pressurized water used to drive the disclosed device.

Likewise, the spherical cleaning means comprising an annular gap which emits a conical jet of high-pressure liquid for cleaning a pipeline surface, disclosed in U.S. Pat. No. 5,296,038, incorporated herein by reference, is suitable for use with the compositions of the present invention. This cleaning device is characterised in that the cleaning means is brought into contact with an inner wall of the line, such that a reduced pressure is established between the cleaning means and the inner wall and the cleaning means is made to move around about the cross-section of the line by twisting the supply conduit about its longitudinal axis. This reduced pressure is preferably established by bringing the annular gap on the cleaning means into close contact with the inner wall of the line and especially by adjusting the cleaning means to assume an angle against the inner wall of the line. The cleaning arrangement is further characterised in that the cleaning means has largely the shape of a ball wherein the continuous gap extends along the outermost periphery of the cleaning means, and a continuous gap is established by the back piece exhibiting an external conical surface extending along its periphery at its forward end, while the front piece presents a conical internal surface corresponding to the back piece of the conical surface in order to, when used, establish an annular gap, with the annular gap being directed back out towards the coupling means at an angle of up to 30–60 degrees.

The sandblasting method of U.S. Pat. No. 5,239,786, incorporated herein by reference, the rotating brush method of U.S. Pat. No. 5,235,718, incorporated herein by reference, the liquid flush/pig launch method of U.S. Pat. No. 4,716,611, incorporated herein by reference, and the pressurized acid method of U.S. Pat. No. 5,045,352, incorporated herein by reference, are all suitable for use in conjunction with the compositions and methods of the present invention.

Furthermore, although it may not qualify strictly as an abrasive cleaning method, the technique for cleaning a cooling tower disclosed in U.S. Pat. No. 4,808,319, incorporated herein by reference, wherein multiple liquid phases flow through the packing material of the tower in a direction counter to the flow of an air phase, is suitable for use in connection with the compositions and methods of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Inhibition Study

The following example demonstrates the inhibitory effect of chelators on species of Aspergillus, Fusarium, Candida, Pseudomonas, vancomycin-resistant enterococci, and multidrug resistant Stenotrophomonas. The data collected are displayed in FIG. 1, FIG. 2, FIG. 3, FIG. 4, FIG. 12, FIG. 13 and FIG. 14. A spectrophotometer was used at a frequency of 660 nanometers (nm) to measure the absorbency of the solution. For molds, all inocula were started at $1\times10^4$ conidia/mL. For yeast and bacteria, all inocula were started at $1\times10^6$ cfu/mL. The medium used was Mueller-Hinton.

The data in FIG. 1 demonstrate an inhibitory effect of EDTA on growth of *Aspergillus flavus* after a 12 hour incubation. FIG. 2 shows a similar effect of EDTA on growth of *Aspergillus terreus*. EDTA is also shown to have a growth inhibitory effect on *Fusarium oxysporum* after 12 h (FIG. 3) and an inhibitory effect on *Candida krusei* that is apparent after only a four hour incubation period (FIG. 4). In addition, EDTA is shown herein to be an effective growth inhibitor of multidrug resistant enterococcus (FIG. 12), multidrug resistant *S. maltophilia* (FIG. 13), and multidrug resistant Pseudomonas (FIG. 14).

EXAMPLE 2

Synergy Study

The following example demonstrates the fungicidal effect of the combination of an antifungal and a chelator. In particular, the studies described herein are directed to determining the presence of a synergistic or additive effect for EDTA and Amphotericin B acting in concert, and for EDTA and Ambisome acting in concert. The studies were conducted in a laboratory incubator at a constant temperature of 30° C. The medium was a single lot of liquid RPMI 1640 medium (Whittaker Bioproducts, Inc., Walkersville, Md.) supplemented with 0.3 g of L-glutamine per liter and 0.165 M MOPS buffer (34.54 g/liter) and without sodium bicarbonate.

Test inocula contained approximately $1\times10^3$ to $1\times10^4$ conidia/mL. To induce conidium and sporangiophore formation, fungi were grown on sabouraud dextrose agar plates at 35° C. for 5 to 7 days. Each fungus was then covered with approximately 2 mL sterile 0.85% saline water. The suspension was then harvested by gently probing the colonies with sterile glass rods. The resulting mixture of conidia or sporangiophores and hyphal fragments was withdrawn and filtered through a sterile 4×4 gauze to a sterile tube. The homogenous suspension was later mixed with a vortex mixer for 30 s and the densities of the suspension were read and adjusted to a range of 80 to 85% transmittance. Inoculum of 0.1 mL was delivered to each flask containing 20 mL of RPMI and drug dilution series. The final conidia concentration ranged from $1\times10^3$ to $1\times10^4$ conidia/mL. A control flask was maintained without any drugs. The flasks were incubated in a shaker at 30° C. for 24 to 48 h. Glass beads were added to all flasks with visible fungal growth in an attempt to homogenize the solution and achieve even distribution of conidia for culture. Cultures were done at 0, 4, 24, and 48 h on sabouraud dextrose agar plates and incubated at 35° C. for 48 h.

Amphotericin B for injection, USP (Gensia Laboratories, Ltd.) was suspended and diluted in sterile water and stored at 1 mg/mL in a glass vile in the dark at −70° C. Ambisome was obtained in 50 mg vials and used immediately upon opening of the vial. Typically, 50 mg of Ambisome was diluted in 12 mL of sterile water. Further dilutions were performed as needed. Edetate disodium INJ., USP (Abbott Laboratories, North Chicago, Ill.) was stored at a concentration of 150 mg/mL at 4° C. Further dilutions were made to achieve the desired concentration of each drug at the time of the study. For Amphotericin B and Ambisome, the concentration was 1.0 μg/mL and for EDTA the concentrations were 0.1 and 1.0 mg/mL.

The data demonstrate the synergistic inhibitory effect of Amphotericin B and EDTA against *A. fumigatus* (FIG. 5 and FIG. 6), against *A. flavus* (FIG. 7 and FIG. 8) and against *Fusarium solani* (FIG. 9). The synergistic effect of a commercially available Amphotericin B formulation, Ambisome, and EDTA against *A. fumigatus* is shown in FIG. 10, and against *Fusarium solani* is shown in FIG. 11.

EXAMPLE 3

Synergy Study

The following example demonstrates a synergistic effect of EDTA and gentamycin or EDTA and polymyxin B against the water-borne microbe *Stenotrophomonas maltophila*. The study was conducted in 15 mL Falcon brand tubes. Seven tubes were filled with 5 mL each of Mueller-Hinton broth; one tube contained EDTA, one tube contained gentamycin, one tube contained polymyxin B, one tube contained EDTA+gentamycin, one tube contained EDTA+polymyxin B, and one tube contained no chelators or antimicrobial agents (as a control). The concentration for each of the active compounds remained constant at 8 μg/mL for gentamycin, 1 mg/mL for EDTA, and 0.5 μg/mL for polymyxin B. The synergistic effects are shown in FIG. 16 for EDTA+gentamycin and FIG. 17 for polymyxin B+EDTA.

EXAMPLE 4

Preparation of Minocycline+EDTA

The present example provides a detailed description of how the minocycline+EDTA preparation is prepared. The minocycline+EDTA solution is prepared as follows so as to achieve a concentration of about 3 mg/mL minocycline and about 30 mg/mL EDTA in a saline solution. Separate solutions of EDTA (60 mg/mL) and minocycline (3 mg/mL) are prepared in saline. The EDTA is reconstituted from 200 mg/mL Edetate Calcium Disodium (Versenste®, 3M Riker, Northridge, Calif.) or reconstituted from Edetate Disodium [150 mg/mL parenteral concentrate (Endtrate®, Abbott, Chicago, Ill., or Disotate®, Forest, Maryland Heights, Mo.)]. Alternatively, the 60 mg/mL of EDTA can be reconstituted from EDTA powder (Sigma Chemical Co., St. Louis, Mo.). Minocycline is obtained from Lederle and combined with a volume of saline sufficient to constitute about 3 mg/mL minocycline. The 6 mg/mL minocycline and 60 mg/mL EDTA solutions are mixed in equal volumes to constitute a 3 mg minocycline and 30 mg EDTA/mL solution.

Once formulated, the minocycline+EDTA may be stored refrigerated at 4° C. until use. It is contemplated that so formulated, the solution will remain chemically stable and active for at least 1 month at 4° C. The preparation is also very stable at room temperature (37° C.) for at least 72 h.

The synergistic effects for EDTA+minocycline against vancomycin-resistant enterococci are shown in FIG. 15.

EXAMPLE 5

Chelating Agent Combinations with Antimicrobial Agents

The present example provides a representative list of specific combinations of ingredients expected for use in the practice of the present invention as a flushing solution. The term antimicrobial agent as used in the description of the present invention includes non-glycopeptide antibiotics and antifungal agents. A representative list of these antimicrobial agents, particularly defined as non-glycopeptide antimicrobial agents, is provided in the general textbook reference of Sanford (1994).

A representative list of antibiotics, chelators and complexing agents that may be used in the preparation of the various embodiments of the invention includes:

Antibiotics
    aminoglycoside
    ampicillin
    carbenicillin
    cefazolin
    cephalosporin
    chloramphenicol
    clindamycin
    erythromycin
    eveninomycin
    gentamycin
    kanamycin
    lipopeptides
    methicillin
    nafcillin
    novobiocia
    oxazolidinones
    penicillin
    polymyxin
    quinolones
    rifampin
    streptogramins
    streptomycin
    sulfamethoxazole
    sulfonamide
    tetracycline
    trimethoprim
    vancomycin
Chelators
    defereoxamine
    dimercaprol
    DMSA
    penicillamine
    succimer
Complexing Agents
    ammonium-1-pyrrolidine dithiocarbanate
    bathophenanthroline
Antiseptic Agents
    chlorhexidine
    silver sulfonamide chlorine bromine Specific combinations contemplated by the inventors include:

EDTA+minocycline

EDTA+minocycline rifampin

EDTA+non-glycopeptide antibiotics (e.g. tetracycline antibiotic+minocycline, doxycycline, oxytetracycline)

Triethylene tetraminedihydrochloride (TTH)+tetracycline antibiotic (minocycline, doxycycline, oxytetracycline)

Hirudin+tetracycline antibiotic (minocycline, doxycycline, oxytetracycline)

Diethylene triamine pentaacetic acid (DTPA)+tetracycline antibiotic (minocycline, doxycycline, oxytetracycline)

Diethylenetriamineacetic acid+tetracycline antibiotic (minocycline, doxycycline, oxytetracycline)

Triethylene tetramine dihydrochloride+tetracycline antibiotic (minocycline, doxycycline, oxytetracycline)

Etidronate® (disodium dihydrogen (1-hydroxyethylidene) bis[phosphonate])+tetracycline antibiotic (minocycline, doxycycline, oxytetracycline)

Dimercaprol+tetracycline antibiotic (minocycline, doxycycline, oxytetracycline).

Citrate+tetracycline antibiotic (minocycline, doxycycline, oxytetracycline).

Methenamine+tetracycline antibiotic (minocycline, doxycycline, oxytetracycline).

EDTA is available as calcium sodium EDTA and sodium EDTA formulations. The most preferred form employed by the present inventors is sodium EDTA. These formulations are provided at a concentration of 150 mg/mL.

As will be appreciated by those of skill in the art, the present list is only intended to be exemplary. Other chelating agents are also expected to be useful in combination with an non-glycopeptide antibiotic or other antimicrobial substance with equal efficacy. In addition, rifampin or any of the rifamycin family of antibiotics, may also be used in the practice of the present invention. These combinations formulated as a coating will preferably further include a material that will enhance adherence or film forming characteristics, of the preparation.

REFERENCES

The following references, to the extent that they provide exemplary procedural or other details supplementary to those set forth herein, are specifically incorporated herein by reference.

Costerton et al., "Bacterial Biofilms in Relation to Internal Corrosion Monitoring and Biocide Strategies", In: *Materials Performance*, p. 49, 1988.

Sanford, et al., In: *Guide to Antimicrobial Therapy*, pp. 118, Table 28, 1994.

U.S. Pat. No. 4,253,971
U.S. Pat. No. 4,297,224
U.S. Pat. No. 4,716,611
U.S. Pat. No. 4,808,319
U.S. Pat. No. 5,045,352
U.S. Pat. No. 5,235,718
U.S. Pat. No. 5,239,786
U.S. Pat. No. 5,296,038
U.S. Pat. No. 5,362,754
U.S. Pat. No. 5,406,666
U.S. Pat. No. 5,449,658
U.S. Pat. No. 5,591,349
U.S. Pat. No. 5,615,696
U.S. patent application Ser. No. 08/317,309

What is claimed is:

1. A method for controlling growth, in an aqueous system, of microorganisms which adhere to walls and other structural surfaces of the system, which method comprises providing to said aqueous system a composition comprising a chelating agent and an antimicrobial compound in an amount at least effective to control said growth.

2. The method of claim 1, wherein said chelating agent is selected from the group consisting of Ethylenediamine-N,N,N',N',-tetraacetic acid, Ethylenediamine-N,N,N',N',-tetraacetic acid, disodium salt, dihydrate, Ethylenediamine-N,N,N',N',-tetraacetic acid, trisodium salt, trihydrate, Ethylenediamine-N,N,N',N'-tetraacetic acid, tetrasodium salt, tetrahydrate, Ethylenefisminr-N,N,N',N'-tetraacetic acid, dipotassium salt, dihydrate, Ethylenediamine-N,N,N',N'-tetraacetic acid, dilithium salt, monhydrate, Ethylenediamine-N,N,N',N'-tetraacetic acid, diammonium salt, Ethylenediamine-N,N,N',N'-tetraacetic acid, tripotassium salt, dihydrate, Ethylenediamine-N,N,N',N'-tetraacetic acid, barium chelate, Ethylenediamine-N,N,N',N'-tetraacetic acid, calcium chelate, Ethylenediamine-N,N,N',N'-tetraacetic acid, cerium chelate, Ethylenediamine-N,N,N',N'-tetraacetic acid, cobalt chelate, Ethylenediamine-N,N,N',N'-tetraacetic acid, copper chelate, Ethylenediamine-N,N,N',N'-tetraacetic acid, dysprosium chelate, Ethylenediamine-N,N,N',N'-tetraacetic acid, europium chelate, Ethylenediamine-N,N,N',N'-tetraacetic acid, iron chelate, Ethylenediamine-N,N,N',N'-tetraacetic acid, indium chelate, Ethylenediamine-N,N,N',N'-tetraacetic acid, lanthanum chelate, Ethylenediamine-N,N,N',N'-tetraacetic acid, magnesium chelate, Ethylenediamine-N,N,N',N'-tetraacetic acid, manganese chelate, Ethylenediamine-N,N,N',N'-tetraacetic acid, nickel chelate, Ethylenediamine-N,N,N',N'-tetraacetic acid, samarium chelate, Ethylenediamine-N,N,N',N'-tetraacetic acid, strontium chelate, Ethylenediamine-N,N,N',N'-tetraacetic acid, zinc chelate, trans-1,2-Diaminocyclohexane-N,N,N',N'-tetraaceticacid, monohydrate, N,N-Bis(2-hydroxyethyl)glycine, 1,3-Diamino-2-hydroxypropane-N,N,N',N'-tetraacetic acid, 1,3-Diaminopropane-N,N,N',N'-tetraacetic acid, Ethylenediamine-N,N'-diacetic acid, Ethylenediamine-N,N'-dipropionic acid dihydrochloride, Ethylenediamine-N,N'-bis(methylenephosphonic acid), hemihydrate, N-(2-Hydroxyethyl)ethylenediamine-N,N,N',N'-triacetic acid, Ethylenediamine-N,N,N',N'-tetrakis(methylenephosponic acid), O,O'-bis(2-aminoethyl)ethyleneglycol-N,N,N',N'-tetraacetic acid, N,N-bis(2-hydroxybenzyl)ethylenediamine-N,N-diacetic acid, 1,6-Hexamethylenediamine-N,N,N',N'-tetraacetic acid, N-(2-Hydroxyethyl)iminodiacetic acid, Iminodiacetic acid, 1,2-Diaminopropane-N,N,N',N'-tetraacetic acid, Nitrilotriacetic acid, Nitrilotripropionic acid, Nitrilotris (methylenephosphoric acid), trisodium salt, 7,19,30-Trioxa-1,4,10,13,16,22,27,33-octaazabicyclo[11,11,11] pentatriacontane, hexahydrobromide and Triethylenetetramine-N,N,N',N",N''',N'''-hexaacetic acid.

3. The method of claim 1, wherein said chelating agent is Ethylenediamine-N,N,N',N',-tetraacetic acid.

4. The method of claim 1, wherein said antimicrobial agent is further defined as an antifungal agent.

5. The method of claim 1, wherein said antifungal agent is selected from the group consisting of UK 109,496 (Voriconazole), Terbinafine, SCH 56592, BF-796, ER 30346, MTCH 24, UK 9746, BTG-137586, UK 9751, RMP-7/Amphotericin B, T 8581, Omoconazole, Flutrimazole, Amphotericin B, Cilofungin LY121019, Nystatin, LY303366 (Echinocandin), Natamycin, L-743872 (pneumocandin), Clotrimazole, Pradimicins (MNS 18184), Miconazole, Benanomicin, Ketoconazole, Ambisome, Terconazole, ABLC, Econazole, Liposomal Amphotericin, Itraconazole, ABCD, Fluconazole, Liposomal Nystatin, Griseofulvin, Nikkomycin Z, and Flucytosine.

6. The method of claim 1, wherein a sufficient amount of said composition is maintained in the aqueous system to inhibit the regrowth of said fungi.

7. The method of claim 1, wherein said composition further comprises an antialgal, antibacterial or antiseptic compound.

8. The method of claim 1, wherein said composition further comprises ortho-phthalaldehyde, glutaraldehyde, or formaldehyde.

9. The method of claim 1, wherein the aqueous system is a recirculating cooling tower, an oil field water flood system, an air washer, or an air conditioning system.

10. The method of claim 1, wherein the aqueous system is used in the manufacture of paper, as a metal working fluid, a heat transfer fluid, a radiator fluid, a cooling system fluid, a conveyor lubricant, an oilfield drilling fluid, or a wastewater processing fluid.

11. A method for controlling, in an aqueous system, the biofouling of the walls and other structural surfaces of the system by a microorganism, said method comprising providing to said system a composition comprising a chelating agent and an antimicrobial agent in an amount at least sufficient to control said biofouling.

12. The method of claim 11, wherein said chelating agent is selected from the group consisting of Ethylenediamine-N,N,N',N',-tetraacetic acid, Ethylenediamine-N,N,N',N',-tetraacetic acid, disodium salt, dihydrate, Ethylenediamine-N,N,N',N',-tetraacetic acid, trisodium salt, trihydrate, Ethylenediamine-N,N,N',N'-tetraacetic acid, tetrasodium salt, tetrahydrate, Ethylenefisminr-N,N,N',N'-tetraacetic acid, dipotassium salt, dihydrate, Ethylenediamine-N,N,N',N'-tetraacetic acid, dilithium salt, monhydrate, Ethylenediamine-N,N,N',N'-tetraacetic acid, diammonium salt, Ethylenediamine-N,N,N',N'-tetraacetic acid, tripotassium salt, dihydrate, Ethylenediamine-N,N,N',N'-tetraacetic acid, barium chelate, Ethylenediamine-N,N,N',N'-tetraacetic acid, calcium chelate, Ethylenediamine-N,N,N',N'-tetraacetic acid, cerium chelate, Ethylenediamine-N,N,N',N'-tetraacetic acid, cobalt chelate, Ethylenediamine-N,N,N',N'-tetraacetic acid, copper chelate, Ethylenediamine-N,N,N',N'-tetraacetic acid, dysprosium chelate, Ethylenediamine-N,N,N',N'-tetraacetic acid, europium chelate, Ethylenediamine-N,N,N',N'-tetraacetic acid, iron chelate, Ethylenediamine-N,N,N',N'-tetraacetic acid, indium chelate, Ethylenediamine-N,N,N',N'-tetraacetic acid, lanthanum chelate, Ethylenediamine-N,N,N',N'-tetraacetic acid, magnesium chelate, Ethylenediamine-N,N,N',N'-tetraacetic acid, manganese chelate, Ethylenediamine-N,N,N',N'-tetraacetic acid, nickel chelate, Ethylenediamine-N,N,N',N'-tetraacetic acid, samarium chelate, Ethylenediamine-N,N,N',N'-tetraacetic acid, strontium chelate, Ethylenediamine-N,N,N',N'-tetraacetic acid, zinc chelate, trans-1,2-Diaminocyclohexane-N,N,N',N'-tetraaceticacid, monohydrate, N,N-Bis(2-hydroxyethyl)glycine, 1,3-Diamino-2-hydroxypropane-N,N,N',N'-tetraacetic acid, 1,3-Diaminopropane-N,N,N',N'-tetraacetic acid, Ethylenediamine-N,N'-diacetic acid, Ethylenediamine-N,N'-dipropionic acid dihydrochloride, Ethylenediamine-N,N'-bis(methylenephosphonic acid), hemihydrate, N-(2-Hydroxyethyl)ethylenediamine-N,N',N'-triacetic acid, Ethylenediamine-N,N,N',N'-tetrakis(methylenephosponic acid), O,O'-bis(2-aminoethyl)ethyleneglycol-N,N,N',N'-tetraacetic acid, N,N-bis(2-hydroxybenzyl) ethylenediamine-N,N-diacetic acid, 1,6-Hexamethylenediamine-N,N,N',N'-tetraacetic acid, N-(2-Hydroxyethyl)iminodiacetic acid, Iminodiacetic acid, 1,2-Diaminopropane-N,N,N',N'-tetraacetic acid, Nitrilotriacetic acid, Nitrilotripropionic acid, Nitrilotris (methylenephosphoric acid), trisodium salt, 7,19,30-Trioxa-1,4,10,13,16,22,27,33 -octaazabicyclo[11,11,11] pentatriacontane, hexahydrobromide and Triethylenetetramine-N,N,N',N'',N''',N'''-hexaacetic acid.

13. The method of claim 12, wherein said chelating agent is Ethylenediamine-N,N,N',N',-tetraacetic acid.

14. The method of claim 11, wherein said antimicrobial agent is further defined as an antifungal agent.

15. The method of claim 11, wherein said antifungal agent is selected from the group consisting of UK 109,496 (Voriconazole), Terbinafine, SCH 56592, BF-796, ER 30346, MTCH 24, UK 9746, BTG-137586, UK 9751, RMP-7/ Amphotericin B, T 8581, Omoconazole, Flutrimazole, Amphotericin B, Cilofungin LY121019, Nystatin, LY303366 (Echinocandin), Natamycin, L-743872 (Pneumocandin), Clotrimazole, Pradimicins (MNS 18184), Miconazole, Benanomicin, Ketoconazole, Ambisome, Terconazole, ABLC, Econazole, Liposomal Amphotericin, Itraconazole, ABCD, Fluconazole, Liposomal Nystatin, Griseofulvin, Nikkomycin Z, and Flucytosine.

16. The method of claim 11, wherein a sufficient amount of said composition is maintained in the aqueous system to inhibit the regrowth of said fungi.

17. The method of claim 11, wherein said composition further comprises an antialgal, antibacterial or antiseptic compound.

18. The method of claim 11, wherein said composition further comprises ortho-phthalaldehyde, glutaraldehyde, or formaldehyde.

19. The method of claim 11, wherein the aqueous system is a recirculating cooling tower, an oil field water flood system, an air washer, or an air conditioning system.

20. The method of claim 11, wherein the aqueous system is used in the manufacture of paper, as a metal working fluid, a heat transfer fluid, a radiator fluid, a cooling system fluid, a conveyor lubricant, an oilfield drilling fluid, or a wastewater processing fluid.

21. A method for removing or reducing formation of a biofilm in an aqueous system comprising providing to said system a composition comprising a chelating agent and an antimicrobial agent in an amount at least sufficient to remove or reduce formation of said biofilm.

22. The method of claim 21, wherein said chelating agent is selected from the group consisting of Ethylenediamine-N,N,N',N',-tetraacetic acid, Ethylenediamine-N,N,N',N',-tetraacetic acid, disodium salt, dihydrate, Ethylenediamine-N,N,N',N',-tetraacetic acid, trisodium salt, trihydrate, Ethylenediamine-N,N,N',N'-tetraacetic acid, tetrasodium salt, tetrahydrate, Ethylenefisminr-N,N,N',N'-tetraacetic acid, dipotassium salt, dihydrate, Ethylenediamine-N,N,N', N'-tetraacetic acid, dilithium salt, monhydrate, Ethylenediamine-N,N,N',N'-tetraacetic, diammonium salt, Ethylenediamine-N,N,N',N'-tetraacetic acid, tripotassium salt, dihydrate, Ethylenediamine-N,N,N',N'-tetraacetic acid, barium chelate, Ethylenediamine-N,N,N',N'-tetraacetic acid, calcium chelate, Ethylenediamine-N,N,N',N'-tetraacetic acid, cerium chelate, Ethylenediamine-N,N,N',N'-tetraacetic acid, cobalt chelate, Ethylenediamine-N,N,N',N'-tetraacetic acid, copper chelate, Ethylenediamine-N,N,N',N'-tetraacetic acid, dysprosium chelate, Ethylenediamine-N,N,N',N'-tetraacetic acid, europium chelate, Ethylenediamine-N,N,N',N'-tetraacetic acid, iron chelate, Ethylenediamine-N,N,N',N'-tetraacetic acid, indium chelate, Ethylenediamine-N,N,N',N'-tetraacetic acid, lanthanum chelate, Ethylenediamine-N,N,N',N'-tetraacetic acid, magnesium chelate, Ethylenediamine-N,N,N',N'-tetraacetic acid, manganese chelate, Ethylenediamine-N,N,N',N'-tetraacetic acid, nickel chelate, Ethylenediamine-N,N,N',N'-tetraacetic acid, samarium chelate, Ethylenediamine-N,N,N',N'-tetraacetic acid, strontium chelate, Ethylenediamine-N,N,N',N'-tetraacetic acid, zinc chelate, trans-1,2-Diaminocyclohexane-N,N,N',N'-tetraaceticacid, monohydrate, N,N-Bis(2-hydroxyethyl)glycine, 1,3-Diamino-2-hydroxypropane-N,N,N',N'-tetraacetic acid, 1,3-Diaminopropane-N,N,N',N'-tetraacetic acid, Ethylenediamine-N,N'-diacetic acid, Ethylenediamine-N,N'-dipropionic acid dihydrochloride, Ethylenediamine-N,N'-bis(methylenephosphonic acid), hemihydrate, N-(2-Hydroxyethyl)ethylenediamine-N,N',N'-triacetic acid, Ethylenediamine-N,N,N',N'-tetrakis(methylenephosponic acid), O,O'-bis(2-aminoethyl)ethyleneglycol-N,N,N',N'-tetraacetic acid, N,N-bis(2-hydroxybenzyl) ethylenediamine-N,N-diacetic acid, 1,6-Hexamethylenediamine-N,N,N',N'-tetraacetic acid, N-(2-Hydroxyethyl)iminodiacetic acid, Iminodiacetic acid, 1,2-Diaminopropane-N,N,N',N'-tetraacetic acid, Nitrilotriacetic acid, Nitrilotripropionic acid, Nitrilotris (methylenephosphoric acid), trisodium salt, 7,19,30-Trioxa-1,4,10,13,16,22,27,33-octaazabicyclo[11,11,11] pentatriacontane, hexahydrobromide and Triethylenetetramine-N,N,N',N'',N''',N'''-hexaacetic acid.

23. The method of claim 22, wherein said chelating agent is Ethylenediamine-N,N,N',N',-tetraacetic acid.

24. The method of claim 11, wherein said antimicrobial agent is further defined as an antifungal agent.

25. The method of claim 21, wherein said antifungal agent is selected from the group consisting of UK 109,496 (Voriconazole), Terbinafine, SCH 56592, BF-796, ER 30346, MTCH 24, UK 9746, BTG-137586, UK 9751, RMP-7/ Amphotericin B, T 8581, Omoconazole, Flutrimazole, Amphotericin B, Cilofungin LY121019, Nystatin, LY303366 (Echinocandin), Natamycin, L-743872 (Pneumocandin), Clotrimazole, Pradimicins (MNS 18184), Miconazole, Benanomicin, Ketoconazole, Ambisome, Terconazole, ABLC, Econazole, Liposomal Amphotericin, Itraconazole, ABCD, Fluconazole, Liposomal Nystatin, Griseofulvin, Nikkomycin Z, and Flucytosine.

26. The method of claim 21, wherein a sufficient amount of said composition is maintained in the aqueous system to inhibit the regrowth of said fungi.

27. The method of claim 21, wherein said composition further comprises an antialgal, antibacterial or antiseptic compound.

28. The method of claim 21, wherein said composition further comprises ortho-phthalaldehyde, glutaraldehyde, or formaldehyde.

29. The method of claim 21, wherein the aqueous system is a recirculating cooling tower, an oil field water flood system, an air washer, or an air conditioning system.

30. The method of claim 21, wherein the aqueous system is used in the manufacture of paper, as a metal working fluid, a heat transfer fluid, a radiator fluid, a cooling system fluid, a conveyor lubricant, an oilfield drilling fluid, or a wastewater processing fluid.

31. A method for inhibiting the growth of a microorganism, comprising contacting said microorganism with a composition comprising a chelating agent and an antimicrobial agent in an amount at least sufficient to inhibit the growth of said microorganism.

32. The method of claim 31, wherein said chelating agent is selected from the group consisting of Ethylenediamine-N,N,N',N',-tetraacetic acid, Ethylenediamine-N,N,N',N',-tetraacetic acid, disodium salt, dihydrate, Ethylenediamine-N,N,N',N',-tetraacetic acid, trisodium salt, trihydrate, Ethylenediamine-N,N,N',N'-tetraacetic acid, tetrasodium salt, tetrahydrate, Ethylenefisminr-N,N,N',N'-tetraacetic acid, dipotassium salt, dihydrate, Ethylenediamine-N,N,N',N'-tetraacetic acid, dilithium salt, monhydrate, Ethylenediamine-N,N,N',N'-tetraacetic acid, diammonium salt, Ethylenediamine-N,N,N',N'-tetraacetic acid, tripotassium salt, dihydrate, Ethylenediamine-N,N,N',N'-tetraacetic acid, barium chelate, Ethylenediamine-N,N,N',N'-tetraacetic acid, calcium chelate, Ethylenediamine-N,N,N',N'-tetraacetic acid, cerium chelate, Ethylenediamine-N,N,N',N'-tetraacetic acid, cobalt chelate, Ethylenediamine-N,N,N',N'-tetraacetic acid, copper chelate, Ethylenediamine-N,N,N',N'-tetraacetic acid, dysprosium chelate, Ethylenediamine-N,N,N',N'-tetraacetic acid, europium chelate, Ethylenediamine-N,N,N',N'-tetraacetic acid, iron chelate, Ethylenediamine-N,N,N',N'-tetraacetic acid, indium chelate, Ethylenediamine-N,N,N',N'-tetraacetic acid, lanthanum chelate, Ethylenediamine-N,N,N',N'-tetraacetic acid, magnesium chelate, Ethylenediamine-N,N,N',N'-tetraacetic acid, manganese chelate, Ethylenediamine-N,N,N',N'-tetraacetic acid, nickel chelate, Ethylenediamine-N,N,N',N'-tetraacetic acid, samarium chelate, Ethylenediamine-N,N,N',N'-tetraacetic acid, strontium chelate, Ethylenediamine-N,N,N',N'-tetraacetic acid, zinc chelate, trans-1,2-Diaminocyclohexane-N,N,N',N'-tetraaceticacid, monohydrate, N,N-Bis(2-hydroxyethyl)glycine, 1,3-Diamino-2-hydroxypropane-N,N,N',N'-tetraacetic acid, 1,3-Diaminopropane-N,N,N',N'-tetraacetic acid, Ethylenediamine-N,N'-diacetic acid, Ethylenediamine-N,N'-dipropionic acid dihydrochloride, Ethylenediamine-N,N'-bis(methylenephosphonic acid), hemihydrate, N-(2-Hydroxyethyl)ethylenediamine-N,N',N'-triacetic acid, Ethylenediamine-N,N,N',N'-tetrakis(methylenephosponic acid), O,O'-bis(2-aminoethyl)ethyleneglycol-N,N,N',N'-tetraacetic acid, N,N-bis(2-hydroxybenzyl) ethylenediamine-N,N-diacetic acid, 1,6-Hexamethylenediamine-N,N,N',N'-tetraacetic acid, N-(2-Hydroxyethyl)iminodiacetic acid, Iminodiacetic acid, 1,2-Diaminopropane-N,N,N',N'-tetraacetic acid, Nitrilotriacetic acid, Nitrilotripropionic acid, Nitrilotris (methylenephosphoric acid), trisodium salt, 7,19,30-Trioxa-1,4,10,13,16,22,27,33-octaazabicyclo[11,11,11] pentatriacontane, hexahydrobromide and Triethylenetetramine-N,N,N',N'',N''',N'''-hexaacetic acid.

33. The method of claim 32, wherein said chelating agent is Ethylenediamine-N,N,N',N',-tetraacetic acid.

34. The method of claim 31, wherein said antimicrobial agent is further defined as an antifungal agent.

35. The method of claim 31, wherein said antifungal agent is selected from the group consisting of UK 109,496 (Voriconazole), Terbinafine, SCH 56592, BF-796, ER 30346, MTCH 24, UK 9746, BTG-137586, UK 9751, RMP-7/ Amphotericin B, T 8581, Omoconazole, Flutrimazole, Amphotericin B, Cilofungin LY121019, Nystatin, LY303366 (Echinocandin), Natamycin, L-743872 (Pneumocandin), Clotrimazole, Pradimicins (MNS 18184), Miconazole, Benanomicin, Ketoconazole, Ambisome, Terconazole, ABLC, Econazole, Liposomal Amphotericin, Itraconazole, ABCD, Fluconazole, Liposomal Nystatin, Griseofulvin, Nikkomycin Z, and Plucytosine.

36. The method of claim 31, wherein a sufficient amount of said composition is maintained in the aqueous system to inhibit the regrowth of said fungi.

37. The method of claim 31, wherein said composition further comprises an antialgal, antibacterial or antiseptic compound.

38. The method of claim 31, wherein said composition further comprises ortho-phthalaldehyde, glutaraldehyde, or formaldehyde.

39. The method of claim 31, wherein the aqueous system is a recirculating cooling tower, an oil field water flood system, an air washer, or an air conditioning system.

40. The method of claim 31, wherein the aqueous system is used in the manufacture of paper, as a metal working fluid, a heat transfer fluid, a radiator fluid, a cooling system fluid, a conveyor lubricant, an oilfield drilling fluid, or a wastewater processing fluid.

41. A method for controlling the growth of microorganisms on the interior surface of a pipe, comprising contacting said surface with a microbicidally-effective amount of a composition comprising an antimicrobial agent and a chelator.

42. The method of claim 41, wherein said chelating agent is selected from the group consisting of Ethylenediamine-N,N,N',N',-tetraacetic acid, Ethylenediamine-N,N,N',N',-tetraacetic acid, disodium salt, dihydrate, Ethylenediamine-N,N,N',N',-tetraacetic acid, trisodium salt, trihydrate, Ethylenediamine-N,N,N',N'-tetraacetic acid, tetrasodium salt, tetrahydrate, Ethylenefisminr-N,N,N',N'-tetraacetic acid, dipotassium salt, dihydrate, Ethylenediamine-N,N,N', N'-tetraacetic acid, dilithium salt, monhydrate, Ethylenediamine-N,N,N',N'-tetraacetic acid, diammonium salt, Ethylenediamine-N,N,N',N'-tetraacetic acid, tripotassium salt, dihydrate, Ethylenediamine-N,N,N',N'-tetraacetic acid, barium chelate, Ethylenediamine-N,N,N',N'-tetraacetic acid, calcium chelate, Ethylenediamine-N,N,N',N'-tetraacetic acid, cerium chelate, Ethylenediamine-N,N,N', N'-tetraacetic acid, cobalt chelate, Ethylenediamine-N,N,N', N'-tetraacetic acid, copper chelate, Ethylenediamine-N,N, N',N'-tetraacetic acid, dysprosium chelate, Ethylenediarine-N,N,N',N'-tetraacetic acid, europium chelate, Ethylenediamine-N,N,N',N'-tetraacetic acid, iron chelate, Ethylenediamine-N,N,N',N'-tetraacetic acid, indium chelate, Ethylenediamine-N,N,N',N'-tetraacetic acid, lanthanum chelate, Ethylenediamine-N,N,N',N'-tetraacetic acid, magnesium chelate, Ethylenediamine-N,N,N',N'-tetraacetic acid, manganese chelate, Ethylenediamine-N,N,N',N'-tetraacetic acid, nickel chelate, Ethylenediamine-N,N,N',N'-tetraacetic acid, samarium chelate, Ethylenediamine-N,N, N',N'-tetraacetic acid, strontium chelate, Ethylenediamine-N,N,N',N'-tetraacetic acid, zinc chelate, trans-1,2-Diaminocyclohexane-N,N,N',N'-tetraaceticacid, monohydrate, N,N-Bis(2-hydroxyetbyl)glycine, 1,3-Diamino-2-hydroxypropane-N,N,N',N'-tetraacetic acid, 1,3-Diaminopropane-N,N,N',N'-tetraacetic acid, Ethylenediamine-N,N'-diacetic acid, Ethylenediamine-N, N'-dipropionic acid dihydrochloride, Ethylenediamine-N, N'-bis(methylenephosphonic acid), hemihydrate, N-(2-Hydroxyethyl)ethylenediamine-N,N',N'-triacetic acid, Ethylenediamine-N,N,N',N'-tetrakis(methylenephosponic acid), O,O'-bis(2-aminoethyl)ethyleneglycol-N,N,N',N'-tetraacetic acid, N,N-bis(2-hydroxybenzyl) ethylenediamine-N,N-diacetic acid, 1,6-Hexamethylenediamine-N,N,N',N'-tetraacetic acid, N-(2-Hydroxyethyl)iminodiacetic acid, Iminodiacetic acid, 1,2-Diaminopropane-N,N,N',N'-tetraacetic acid, Nitrilotriacetic acid, Nitrilotripropionic acid, Nitrilotris (methylenephosphoric acid), trisodium salt, 7,19,30-Trioxa-1,4,10,13,16,22,27,33-octaazabicyclo[11,11,11] pentatriacontane, hexahydrobromide and Triethylenetetramine-N,N,N',N'',N''',N'''-hexaacetic acid.

43. The method of claim 42, wherein said chelating agent is Ethylenediamine-N,N,N',N',tetraacetic acid.

44. The method of claim 41, wherein said antimicrobial agent is further defined as an antifungal agent.

45. The method of claim 41, wherein said antifungal agent is selected from the group consisting of UK 109,496 (Voriconazole), Terbinafine, SCH 56592, BF-796, ER 30346, MTCH 24, UK 9746, BTG-137586, UK 9751, RMP-7/ Amphotericin B, T 8581, Omoconazole, Flutrimazole, Amphotericin B, Cilofungin LY121019, Nystatin, LY303366 (Echinocandin), Natamycin, L-743872 (Pneumocandin), Clotrimazole, Pradimicins (MNS 18184), Miconazole, Benanomicin, Ketoconazole, Ambisome, Terconazole, ABLC, Econazole, Liposomal Amphotericin, Itraconazole, ABCD, Fluconazole, Liposomal Nystatin, Griseofulvin, Nikkomycin Z, and Flucytosine.

46. The method of claim 41, wherein a sufficient amount of said composition is maintained in the aqueous system to inhibit the regrowth of said fungi.

47. The method of claim 41, wherein said composition further comprises an antialgal, antibacterial or antiseptic compound.

48. The method of claim 41, wherein said composition further comprises ortho-phthalaldehyde, glutaraldehyde, or formaldehyde.

49. The method of claim 41, wherein the aqueous system is a recirculating cooling tower, an oil field water flood system, an air washer, or an air conditioning system.

50. The method of claim 41, wherein the aqueous system is used in the manufacture of paper, as a metal working fluid, a heat transfer fluid, a radiator fluid, a cooling system fluid, a conveyor lubricant, an oilfield drilling fluid, or a wastewater processing fluid.

51. A method for inhibiting the growth of a bacterium, comprising contacting said bacterium with a composition comprising a chelating agent and an antibiotic in an amount at least sufficient to inhibit the growth of said bacterium.

52. A method for controlling the growth of bacteria on the interior surface of a pipe, comprising contacting said surface with a bactericidally-effective amount of a composition comprising an antibiotic and a chelator.

53. A method for inhibiting the growth of a fungus, comprising contacting said fungus with a composition comprising a chelating agent and an antifungal agent in an amount at least sufficient to inhibit the growth of said fungus.

54. A method for controlling the growth of fungi on the interior surface of a pipe, comprising contacting said surface with a fungicidally-effective amount of a composition comprising an antifungal agent and a chelator.

* * * * *

UNITED STATES PATENT AND TRADEMARK OFFICE
CERTIFICATE OF CORRECTION

PATENT NO.    : 6,267,979 B1
DATED         : July 31, 2001
INVENTOR(S)   : Raad et al.

It is certified that error appears in the above-identified patent and that said Letters Patent is hereby corrected as shown below:

Column 20,
Line 19, please delete "monhydrate" and insert -- monohydrate -- therefor.
Line 64, please delete "claim 1" and insert -- claim 4 -- therefor.

Column 21,
Line 4, please delete "(pneumocandin)" and insert -- (Pneumocandin) -- therefor.
Line 40, please delete "monhydrate" and insert -- monohydrate -- therefor.

Column 22,
Line 18, please delete "claim 11" and insert -- claim 14 -- therefor.
Line 60, please delete "monhydrate" and insert -- monohydrate -- therefor.

Column 23,
Line 37, please delete "claim 21" and insert -- claim 24 -- therefor.

Column 24,
Line 12, please delete "monhydrate" and insert -- monohydrate -- therefor.
Line 67, please delete "Plucytosine" and insert -- Flucytosine -- therefor.

Column 25,
Line 31, please delete "monhydrate" and insert -- monohydrate -- therefor.

Column 26,
Line 11, please delete "N,N,N',N',tetraacetic acid" and insert -- N,N,N',N',-tetraacetic acid -- therefor.

Signed and Sealed this

Thirtieth Day of July, 2002

Attest:

*Attesting Officer*

JAMES E. ROGAN
*Director of the United States Patent and Trademark Office*